United States Patent
Ge et al.

(10) Patent No.: US 10,314,648 B2
(45) Date of Patent: Jun. 11, 2019

(54) COAXIAL ABLATION PROBE AND METHOD AND SYSTEM FOR REAL-TIME MONITORING OF ABLATION THERAPY

(71) Applicant: The Trustees of the University of Pennsylvania, Philadelphia, PA (US)

(72) Inventors: Benjamin Hairan Ge, Philadelphia, PA (US); Maxim Itkin, Bala Cynwyd, PA (US); Charles Nicholas Weber, Philadelphia, PA (US)

(73) Assignee: The Trustees of the Universoty of Pennsylvania, Philadelphia, PA (US)

( * ) Notice: Subject to any disclaimer, the term of this patent is extended or adjusted under 35 U.S.C. 154(b) by 360 days.

(21) Appl. No.: 15/104,142

(22) PCT Filed: Dec. 15, 2014

(86) PCT No.: PCT/US2014/070372
§ 371 (c)(1),
(2) Date: Jun. 13, 2016

(87) PCT Pub. No.: WO2015/089505
PCT Pub. Date: Jun. 18, 2015

(65) Prior Publication Data
US 2016/0317212 A1     Nov. 3, 2016

Related U.S. Application Data

(60) Provisional application No. 61/915,962, filed on Dec. 13, 2013.

(51) Int. Cl.
*A61B 18/14* (2006.01)
*A61B 18/00* (2006.01)
*A61B 90/00* (2016.01)

(52) U.S. Cl.
CPC ............ *A61B 18/148* (2013.01); *A61B 90/37* (2016.02); *A61B 2018/00267* (2013.01);
(Continued)

(58) Field of Classification Search
CPC ........ A61B 18/148; A61B 2018/00267; A61B 2018/00529; A61B 2018/00577;
(Continued)

(56) References Cited

U.S. PATENT DOCUMENTS 5,647,361 A     7/1997  Damadian
6,006,755 A  *  12/1999 Edwards ................ A61B 18/00
                                                     128/898
(Continued)

FOREIGN PATENT DOCUMENTS

WO    WO 2012/177586 A1    12/2012

OTHER PUBLICATIONS

Ahmed et al., "Principles of and advances in percutaneous ablation," Radiology, 258(2):351-369 (2011).
(Continued)

*Primary Examiner* — Michael F Peffley
(74) *Attorney, Agent, or Firm* — Jenkins, Wilson, Taylor & Hunt, P.A.

(57) ABSTRACT

The subject matter described relates to a coaxial ablation probe and method and system for real time monitoring of ablation progress for percutaneous ablation. The probe includes an anode. The probe further includes a size and shape adjustable cathode cage surrounding the anode, the cathode cage includes a plurality of struts. The anode extends coaxially with respect to the struts that form the cathode cage. The cathode cage defines the treatment volume. Probe insertion and ablation progress will be monitored by a magnetic resonance imaging system.

27 Claims, 25 Drawing Sheets

(52) U.S. Cl.
CPC .............. *A61B 2018/00529* (2013.01); *A61B 2018/00577* (2013.01); *A61B 2018/144* (2013.01); *A61B 2018/1472* (2013.01); *A61B 2018/1475* (2013.01); *A61B 2090/374* (2016.02); *A61B 2218/002* (2013.01)

(58) Field of Classification Search
CPC ...... A61B 2018/144; A61B 2018/1472; A61B 2018/1475
See application file for complete search history.

(56) References Cited

U.S. PATENT DOCUMENTS

| | | | |
|---|---|---|---|
| 6,066,125 A | | 5/2000 | Webster, Jr. |
| 6,093,185 A * | | 7/2000 | Ellis .................... A61B 18/1477 606/28 |
| 6,632,222 B1 * | | 10/2003 | Edwards ............ A61B 18/1477 606/41 |
| 6,712,814 B2 * | | 3/2004 | Edwards ............ A61B 5/04884 128/898 |
| 7,175,829 B2 | | 2/2007 | Lauffer et al. |
| 7,792,566 B2 * | | 9/2010 | Roland .................. A61B 5/055 600/407 |
| 7,875,025 B2 * | | 1/2011 | Cockburn ............ A61B 8/0841 606/41 |
| 8,080,009 B2 | | 12/2011 | Lee et al. |
| 8,090,449 B2 | | 1/2012 | King et al. |
| 8,282,631 B2 | | 10/2012 | Davalos et al. |
| 8,337,492 B2 * | | 12/2012 | Kunis ................ A61B 18/1815 606/41 |
| 8,396,532 B2 | | 3/2013 | Jenkins et al. |
| 8,548,567 B2 | | 10/2013 | Maschke et al. |
| 8,562,588 B2 | | 10/2013 | Hobbs et al. |
| 2010/0025069 A1 | | 2/2010 | Smith, III |
| 2010/0174280 A1 | | 7/2010 | Grimaldi |
| 2011/0144576 A1 | | 6/2011 | Rothe et al. |
| 2012/0101362 A1 * | | 4/2012 | Weiss ................ A61M 25/0021 600/411 |
| 2014/0025069 A1 * | | 1/2014 | Willard .............. A61B 18/1492 606/41 |

OTHER PUBLICATIONS

Knavel et al., "Tumor ablation: common modalities and general practices," Techniques in vascular and interventional radiology, 16(4), pp. 192-200 (2013).
Jahangeer et al., "Review of current thermal ablation treatment for lung cancer and the potential of electrochemotherapy as a means for treatment of lung tumours," Cancer treatment reviews, 39(8), pp. 862-871 (2013).
Antoch et al., "Value of CT volume imaging for optimal placement of radiofrequency ablation probes in liver lesions," Journal of vascular and interventional radiology, JVIR.13(11), pp. 1155-1161 (2002).
Rose et al., "Value of three-dimensional US for optimizing guidance for ablating focal liver tumors," Journal of vascular and Interventional radiology JVIR, 12(4), pp. 507-515 (2001).
Leveillee et al., "Emerging needle ablation technology in urology," Current opinion in urology, vol. 24, No. 1, Lippincott Williams & Wilkins, pp. 98-103, (Copyright 2013).
Ierardi et al., "Microwave ablation of liver metastases to overcome the limitations of radiofrequency ablation," La Radiologia medica, 118(6), pp. 949-961 (2013).
Fabiano et al., "Laser-interstitial thermal therapy for refractory cerebral edema from post-radiosurgery metastasis," World neurosurgery, pp. 652.e1-652.e4 (2013).
Ellis et al., "Clinical applications for magnetic resonance guided high intensity focused ultrasound (MRgHIFU): present and future," Journal of medical imaging and radiation oncology, 57(4), pp. 391-399 (2013).

Jensen et al., "Real-time temperature estimation and monitoring of HIFU ablation through a combined modeling and passive acoustic mapping approach," Physics in medicine and biology, 58(17), pp. 5833-5850 (2013).
Passera et al., "Radiofrequency ablation of liver tumors: quantitative assessment of tumor coverage through CT image processing. BMC medical imaging," 13:3, pp. 1-10 (2013).
Robertson et al., "Experimental study of electrolysis-induced hepatic necrosis," The British Journal of Surgery, 85(9), pp. 1212-1216 (1998).
Wemyss-Holden et al., "Electrolytic ablation as an adjunct to liver resection: Safety and efficacy in patients," ANZ journal of surgery, 70(8), pp. 589-593 (2002).
Wemyss-Holden et al., "The safety of electrolytically induced hepatic necrosis in a pig model," The Australian and New Zealand journal of surgery, 70(8), pp. 607-612 (2000).
Wemyss-Holden et al., "Electrolytic ablation as an adjunct to liver resection: experimental studies of predictability and safety," The British journal of surgery, 89(5), pp. 579-585 (2002).
Wemyss-Holden et al., "Electrochemical lesions in the rat liver support its potential for treatment of liver tumors," The Journal of surgical research, 93(1), pp. 55-62 (2000).
Wemyss-Holden et al., "A new treatment for unresectable liver tumours: long-term studies of electrolytic lesions in the pig liver," Clinical science, 98(5), pp. 561-567 (2000).
Wemyss-Holden et al., "Electrolytic treatment of colorectal liver tumour deposits in a rat model: a technique with potential for patients with unresectable liver tumours," Digestive diseases, 18(2), pp. 50-57 (2000).
Finch et al., "Liver electrolysis: pH can reliably monitor the extent of hepatic ablation in pigs," Clinical science, 102(4), pp. 389-395 (2002).
Fosh et al., "Use of electrolysis for the treatment of non-resectable hepatocellular carcinoma," ANZ journal of surgery, 73(12), pp. 1068-1070 (2003).
Nilsson et al., "Electrochemical treatment of tumours," Bioelectrochemistry, 51(1), pp. 1-11 (2000).
Von Euler et al., "Electrochemical treatment (EChT) effects in rat mammary and liver tissue," In vivo optimizing of a dose-planning model for EChT of tumours. Bioelectrochemistry, 54(2), pp. 117-124 (2001).
Von Euler et al., "Animal models for treatment of unresectable liver tumours: a histopathologic and ultra-structural study of cellular toxic changes after electrochemical treatment in rat and dog liver," Bioelectrochemistry, 59(1-2), pp. 89-98 (2003).
Von Euler et al., "Cellular toxicity induced by different pH levels on the R3230AC rat mammary tumour cell line. An in vitro model for investigation of the tumour destructive properties of electrochemical treatment of tumours," Bioelectrochemistry, 58(2), pp. 163-170 (2002).
Martin et al., "Meta-analysis of cryoablation versus microwave ablation for small renal masses: is there a difference in outcome?" Diagnostic and interventional radiology, 19(6), pp. 501-507 (2013).
Autorino et al., "Cryoablation for small renal tumors:current status and future perspectives," Urologic oncology, 30(4 Suppl), pp. S20-S27 (2012).
Paiva et al., "Update on laser photochemotherapy: an alternative for cancer treatment," Anti-cancer agents in medicinal chemistry, 11(8):772-779 (2011).
Froeling et al., "Outcome of uterine artery embolization versus MR-guided high-intensity focused ultrasound treatment for uterine fibroids: Long-term results," European journal of radiology, 82(12), pp. 2265-2269 (2013).
Jenne et al., "High-intensity focused ultrasound: principles, therapy guidance, simulations and applications," Zeitschrift fur medizinische Physik, 22(4), pp. 311-322 (2012).
Napoli et al., "Real-time magnetic resonance-guided high-intensity focused ultrasound focal therapy for localised prostate cancer: preliminary experience," European urology, 63(2), pp. 395-398 (2013).
Bruix et al., "Focus on hepatocellular carcinoma," Cancer cell, 5(3), pp. 215-219 (2013).

(56) References Cited

OTHER PUBLICATIONS

Samuelsson et al., Abstract of "Electrolytic destruction of lung tissue in the rabbit," Acta radiologica: diagnosis, 21(4), p. 1(1980).
Griffin et al., "The effects of low-level direct current therapy on a preclinical mammary carcinoma: tumour regression and systemic biochemical sequelae," British journal of cancer, 69(5), pp. 875-878 (1994).
Griffin et al., "Low-level direct electrical current therapy for hepatic metastases. I. Preclinical studies on normal liver," British journal of cancer, 72(1):31-34 (1995).
Nilsson et al., "Mathematical modelling of physicochemical reactions and transport processes occurring around a platinum cathode during the electrochemical treatment of tumours," Bioelectrochemistry,53(2), pp. 213-224 (2001).
Lin et al., "Saturated saline enhances the effect of electrochemical therapy," Digestive diseases and sciences, 45(3):509-514 (2000).
Chou et al., "Electrochemical treatment of mouse and rat fibrosarcomas with direct current," Bioelectromagnetics,18(1), pp. 14-24 (1997).
Li et al., "Effects of direct current on dog liver: possible mechanisms for tumor electrochemical treatment," Bioelectromagnetics, 18(1), pp. 2-7 (1997).
Ciria et al., "Antitumor effectiveness of different amounts of electrical charge in Ehrlich and fibrosarcoma Sa-37 tumors," BMC cancer, 4:87, pp. 1-10 (2004).
Ciria et al., "Antitumor effects of electrochemical treatment," Chinese journal of cancer research, 25(2), pp. 1-14 (2013).
Schroeppel et al., "Direct current ablation destroys multi-stage fibrosarcomas in rats," Conference proceedings: Annual International Conference of the IEEE Engineering in Medicine and Biology Society 2009, pp. 3099-3104 (2009).
Czymek et al., "Electrochemical treatment: An investigation of dose-response relationships using an isolated liver perfusion model," Saudi journal of gastroenterology: official journal of the Saudi Gastroenterology Association, 17(5), pp. 11 (2011).
Brown et al., "Interventional radiology and the pancreatic cancer patient," Cancer Journal, 18(6), pp. 591-601 (2012).
Yu et al., "Therapeutic potential of irreversible electroporation in sarcoma," Expert review of anticancer therapy, 12(2), pp. 177-184 (2012).
Appelbaum et al., "Irreversible Electroporation Ablation: Creation of Large-Volume Ablation Zones in in Vivo Porcine Liver with Four-Electrode Arrays," Radiology, pp. 416-424 (2013).
Niessen et al., "Irreversible electroporation of a hepatocellular carcinoma lesion adjacent to a transjugular intrahepatic portosystemic shunt stent graft," Korean journal of radiology: official journal of the Korean Radiological Society,14(5), pp. 797-800 (2013).
Martin, "Irreversible electroporation of locally advanced pancreatic head adenocarcinoma," Journal of gastrointestinal surgery: official journal of the Society for Surgery of the Alimentary Tract, 17(10):1850-1856 (2013).
Ben-David et al., "Characterization of irreversible electroporation ablation in in vivo porcine liver," AJR American journal of roentgenology, 198(1), pp. W62-W68 (2012).
Ben-David et al., "Irreversible electroporation: treatment effect is susceptible to local environment and tissue properties," Radiology, 269(3), pp. 738-747 (2013).
Lu et al., "Irreversible electroporation: ready for prime time?" Techniques in vascular and interventional radiology, 16(4), pp. 277-286 (2013).
Guo et al., "Irreversible electroporation in the liver: contrast-enhanced inversion-recovery MR imaging approaches to differentiate reversibly electroporated penumbra from irreversibly electroporated ablation zones," Radiology, 258(2), pp. 461-468 (2011).
Ormiga et al., "An initial investigation of the electrochemical dissolution of fragments of nickel-titanium endodontic files," Journal of endodontics, 37(4), pp. 526-530 (2011).
Castleman et al., "Biocompatibility of nitinol alloy as an implant material," Journal of biomedical materials research, 10(5), pp. 695-731 (1976).
Civjan et al., "Potential applications of certain nickel-titanium (nitinol) alloys," Journal of dental research, 54(1), pp. 89-96 (1975).
Simon et al., "A vena cava filter using thermal shape memory alloy," Experimental aspects Radiology, 125(1), pp. 89-94 (1977).
Girard et al., "Wallstent metallic biliary endoprosthesis: MR imaging characteristics," Radiology, 184(3), pp. 874-876 (1992).
Buehler et al., "Effects of low-temperature phase changes on the mechanical properties of alloys near composition TiNi," J Appl Phys, 34:3, pp. 1475-1477 (1963).
Wang et al., "Crystal structure and a unique martensitic transition of TiNi," J Appl Phys, 36:8, pp. 3232-3239 (1965).
Correa-Gallego et al., "A Retrospective Comparison of Microwave Ablation vs. Radiofrequency Ablation for Colorectal Cancer Hepatic Metastases," Ann Surg Oncol, 21(13), pp. 1-11 (2014).
Notification of Transmittal of the International Search Report and the Written Opinion of the International Searching Authority, or the Declaration for International Application No. PCT/US14/70372 (dated Mar. 16, 2015).

* cited by examiner

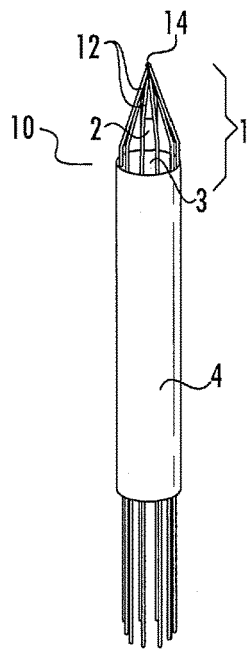
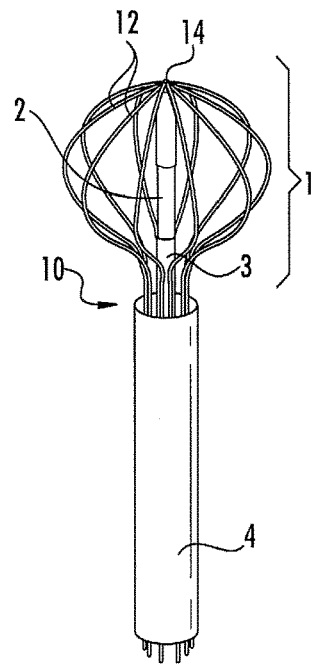
FIG. 2A    FIG. 2B
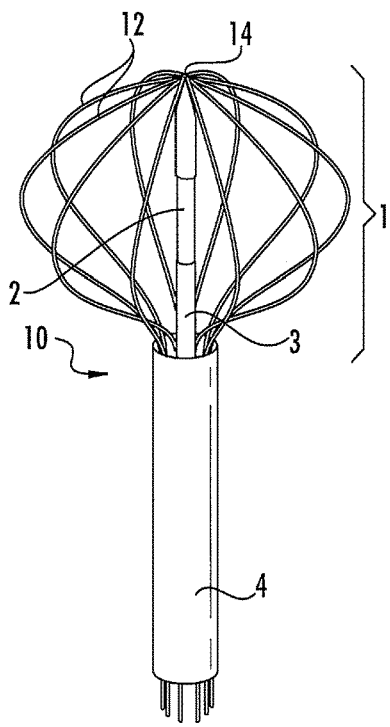
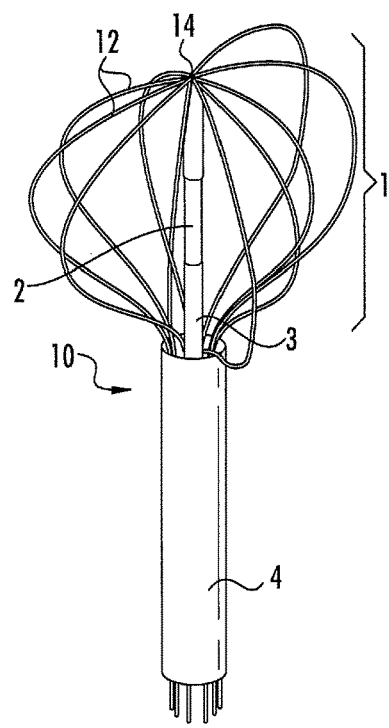
FIG. 2C    FIG. 2D

T2 MRI SIGNAL CHANGES CORRESPOND TO GROSS PATHOLOGY

COAXIAL ABLATION PROBE AND METHOD AND SYSTEM FOR REAL-TIME MONITORING OF ABLATION THERAPY

1. PRIORITY CLAIM

This application claims the benefit of U.S. Provisional Application Ser. No. 61/915,962, filed Dec. 13, 2013, the disclosure of which is incorporated herein by reference in its entirety.

2. TECHNICAL FIELD

The presently disclosed subject matter relates to novel devices and methods for performing and real-time monitoring of ablation therapy, including, but not limited to electrochemical treatment (EChT). EChT is a percutaneous ablation technique utilizing direct current (DC) electricity to create toxic products to destroy abnormal tissue. The presently disclosed subject matter also relates to a coaxial ablation probe for EChT and/or other ablation techniques, including thermal ablation and irreversible electroporation.

3. BACKGROUND

Minimally invasive techniques for treating abnormal tissue have become widely accepted alternatives to surgery, especially with respect to liver tumors. Interventional radiologists can choose from a variety of percutaneous ablation devices that destroy abnormal tissue by delivering energy through needle-like probes placed through the skin. However, the current ablation technology is limited by an inability to monitor therapy in real-time, a high local recurrence rate, a need for multiple probes to treat larger tumors, and a risk of damage to adjacent structures.

4. SUMMARY

The presently disclosed subject matter relates to, in part, methods of employing magnetic resonance to perform real-time monitoring of ablation therapy, including, but not limited to EChT. In certain embodiments, the EChT-mediated ablation monitored by magnetic resonance is achieved using a coaxial ablation probe comprising an anode nested within an adjustable cathode cage.

The subject matter described relates to a coaxial ablation probe for percutaneous ablation. The probe includes an anode. The probe further includes a cathode cage surrounding the anode, the cathode cage includes a plurality of struts. The anode extends coaxially with respect to the struts that form the cathode cage. The cathode cage defines the treatment volume.

5. BRIEF DESCRIPTIONS OF THE DRAWINGS

FIGS. 1A and 1B depict: (A) Axial T2 MRI of rabbit VX2 papilloma electrochemical treatment. The low signal intensity about the electrode represents gas formation. The sharply marginated T2 signal has nearly identical contours as the necrosis (B) seen on gross pathology. The same indentation is marked by the arrow;

Figure 1A:
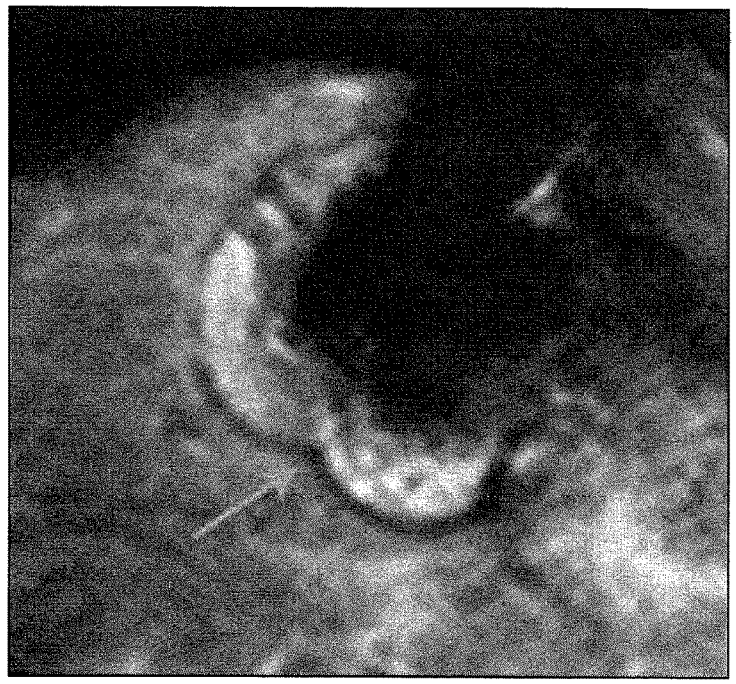
Figure 1B:
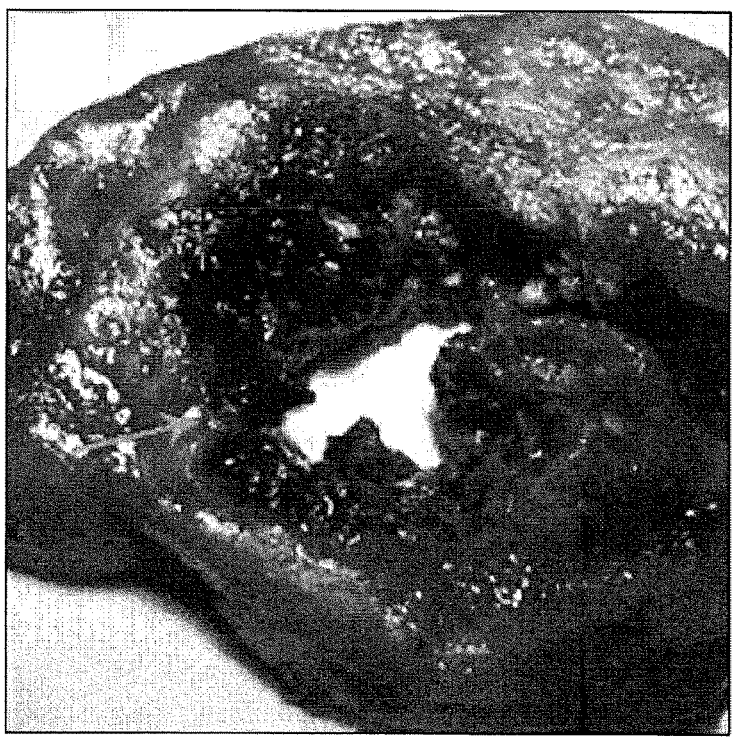
Figure 2E:
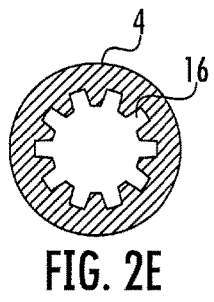
FIGS. 2E-2I illustrate different configurations for an outer sheath for a coaxial ablation probe according to an embodiment of the subject matter described herein.
Figure 2F:
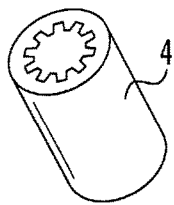
Figure 2G:
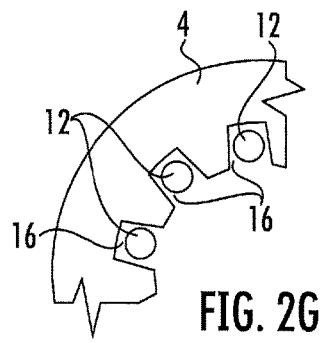
Figure 2H:
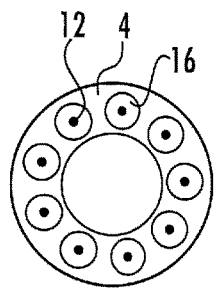
Figure 2I:
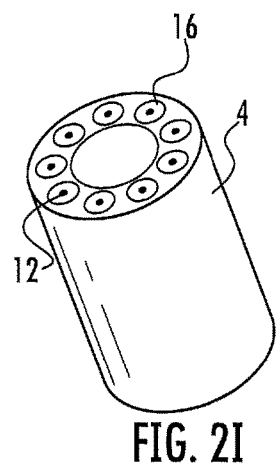
Figure 2J:
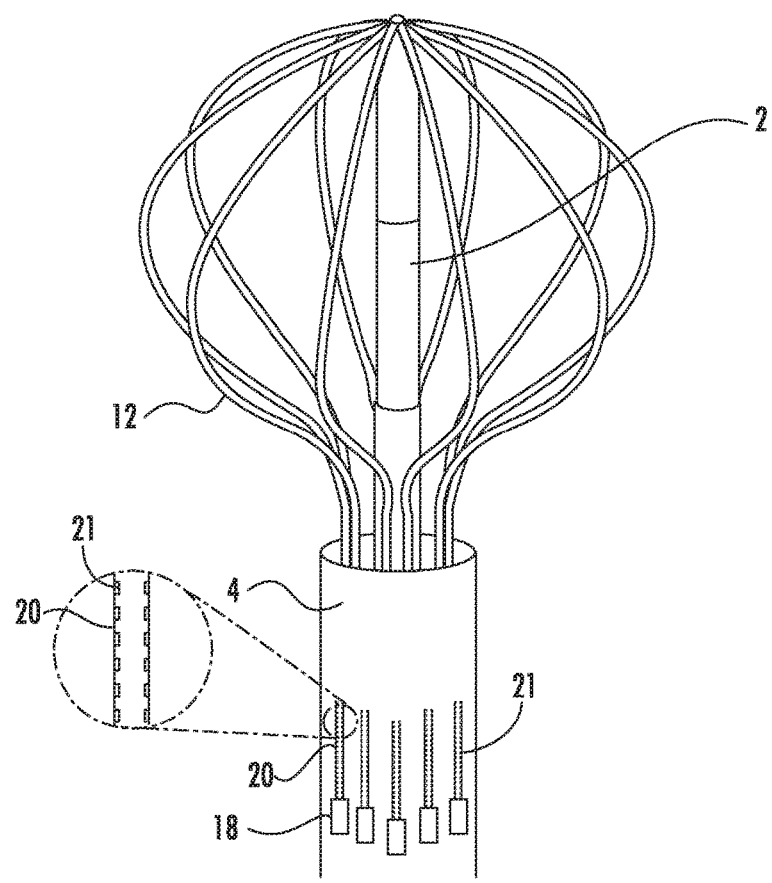
FIGS. 2J-2M illustrate different views of an actuator and corresponding channels or slots for moving individual struts of a coaxial ablation probe according to an embodiment of the subject matter described herein.
Figure 2K:
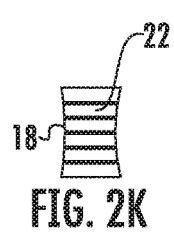
Figure 2L:
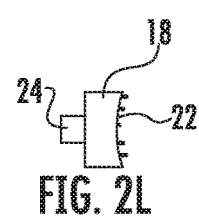
Figure 2M:
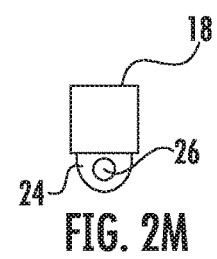
Figure 2N:
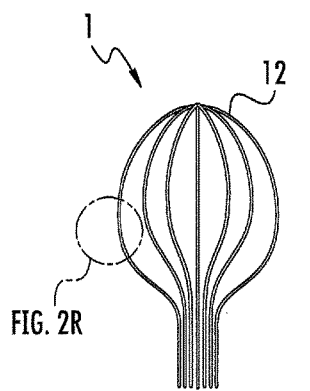
FIGS. 2N-2Q illustrate different embodiments of a cathode cage for a coaxial ablation probe according to an embodiment of the subject matter described herein.
Figure 2R:
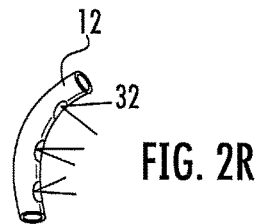
FIGS. 2R-2V illustrate different strut cross sections for a coaxial ablation probe according to an embodiment of the subject matter described herein.
Figure 2O:
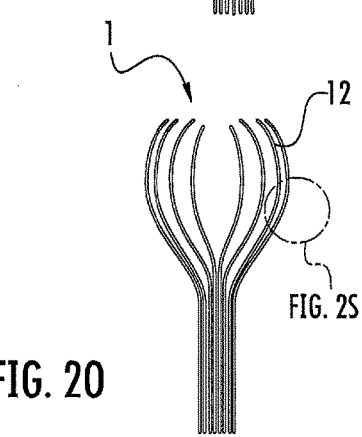
Figure 2S:
Figure 2T:
Figure 2P:
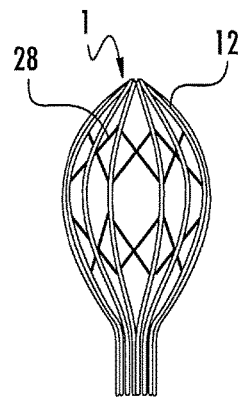
Figure 2U:
Figure 2V:
Figure 2Q:
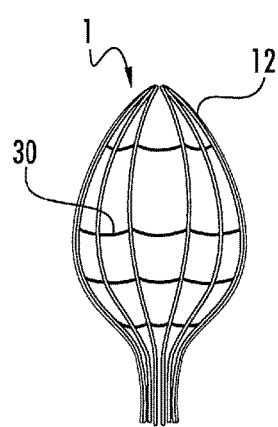
Figure 2A:
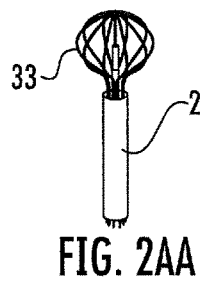
FIG. 2A-2D illustrates a coaxial ablation probe in various different states according to embodiments of the subject matter described herein.
Figure 3:
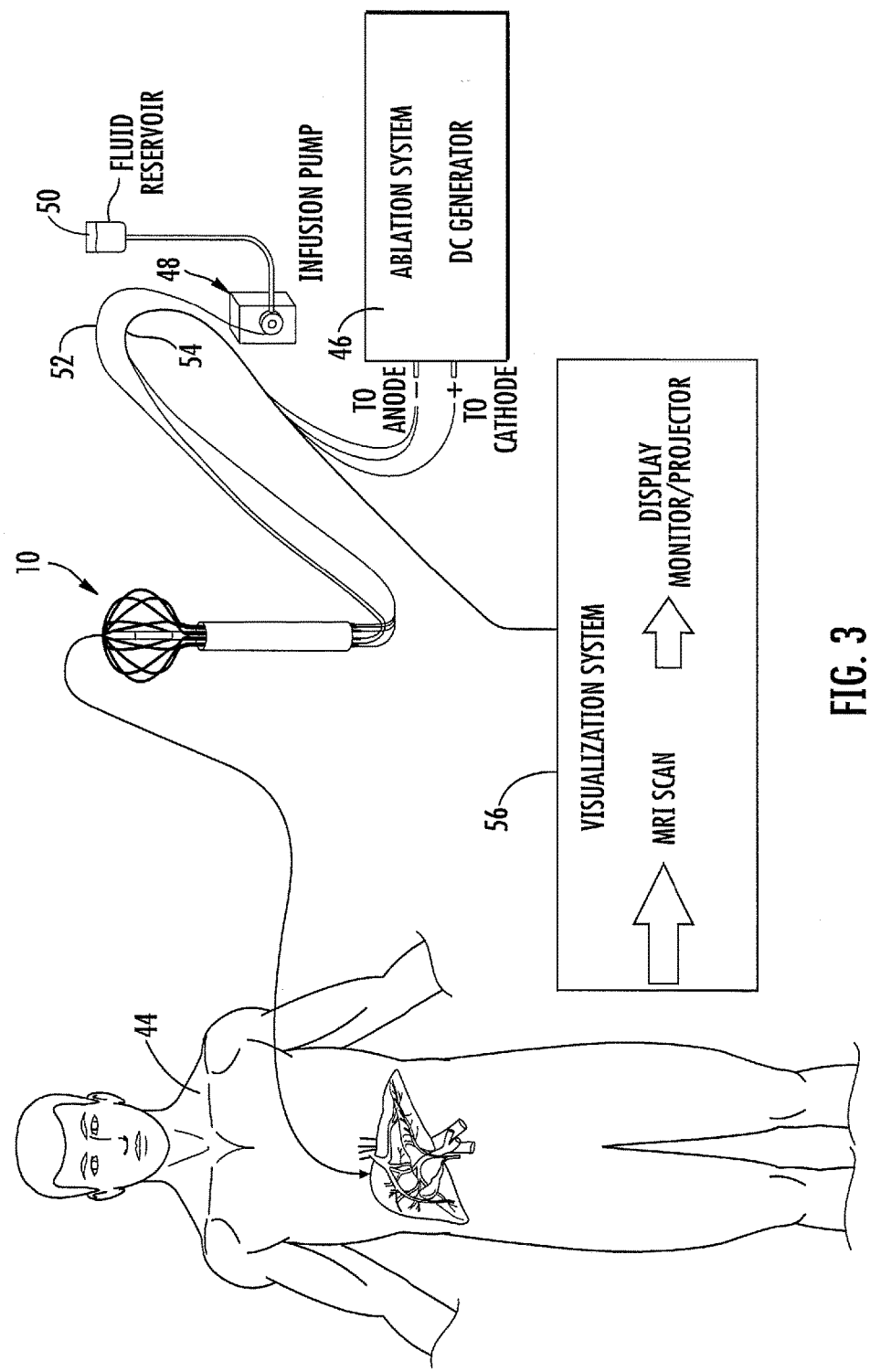
Figure 4:
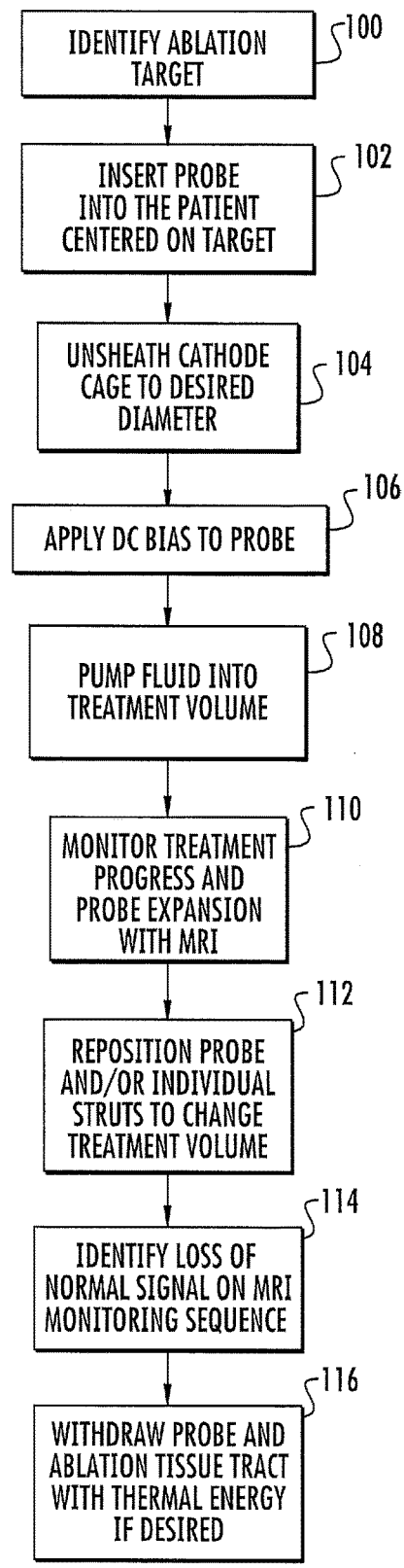
Figure 6A:
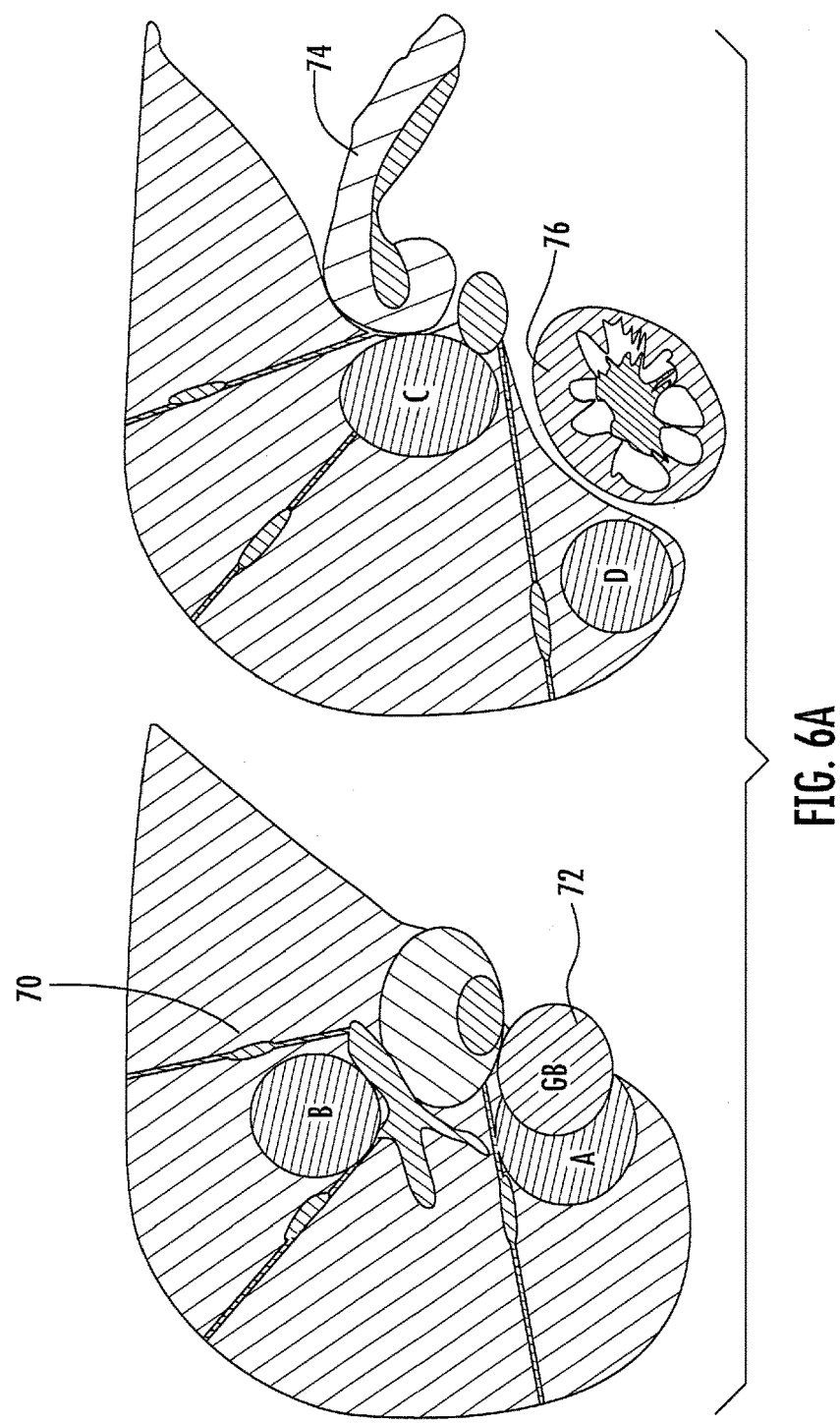
Figure 6B:
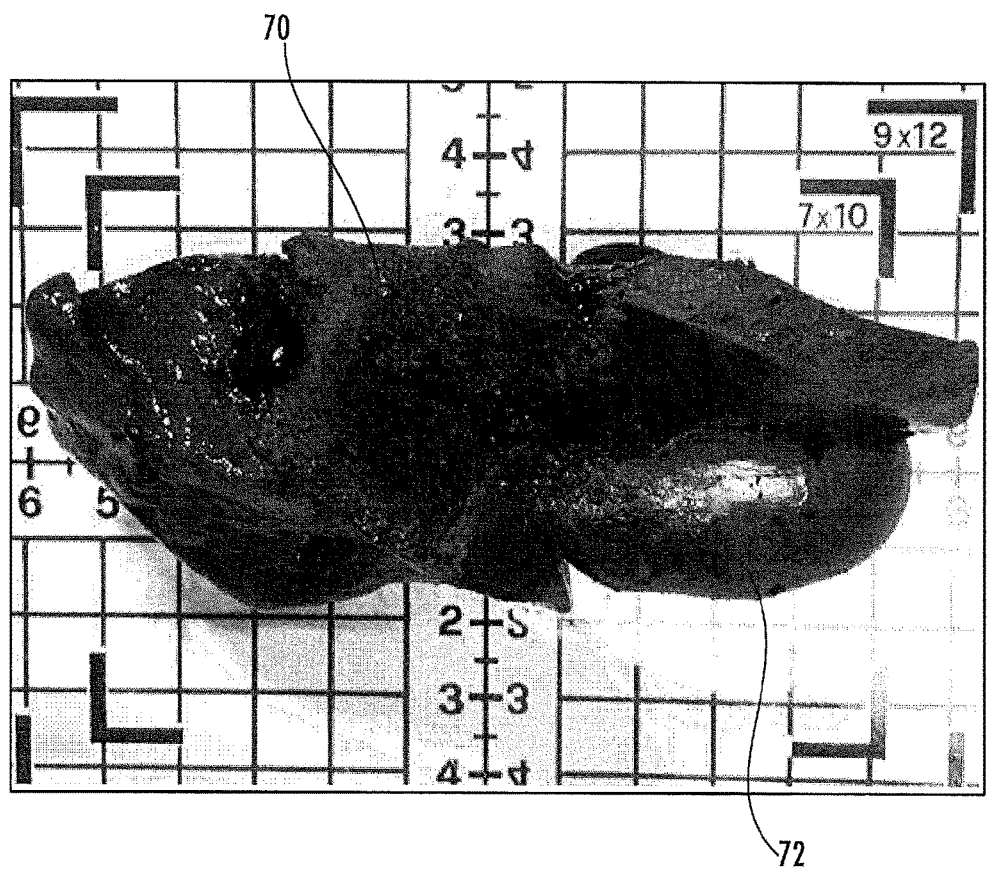
Figure 7:
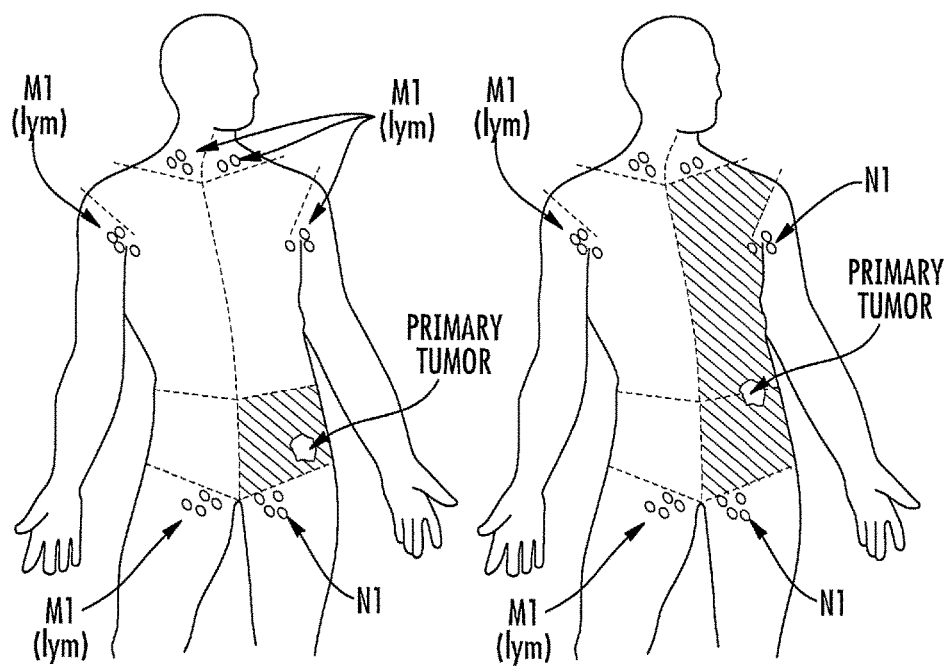
Figure 9A:
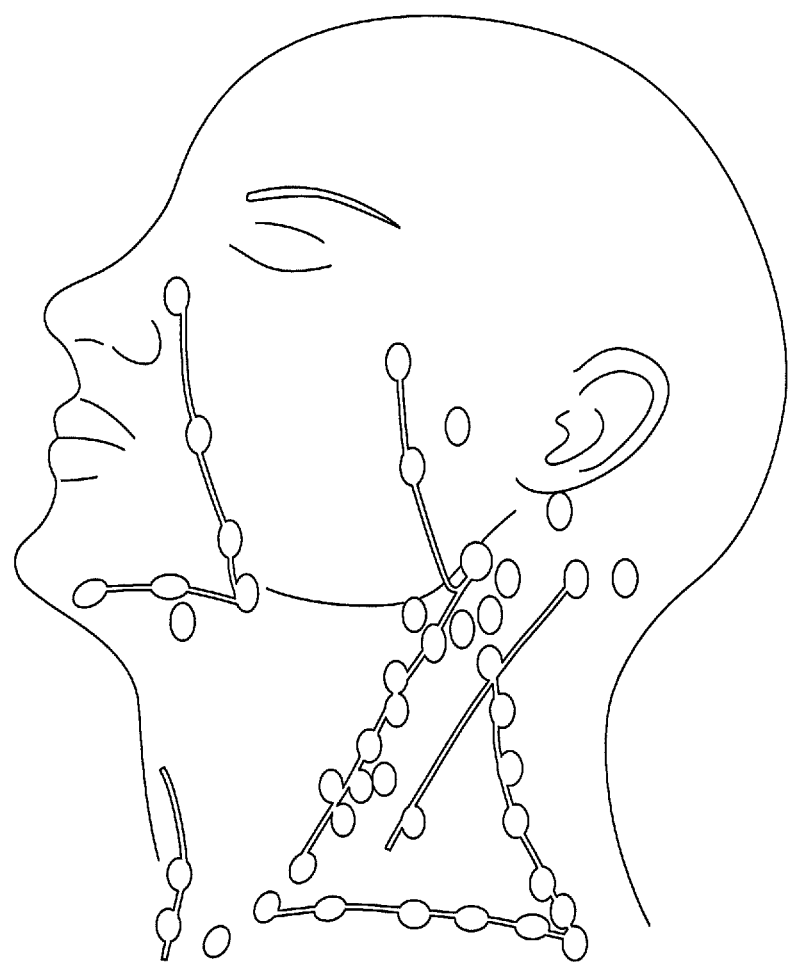
Figure 9B:
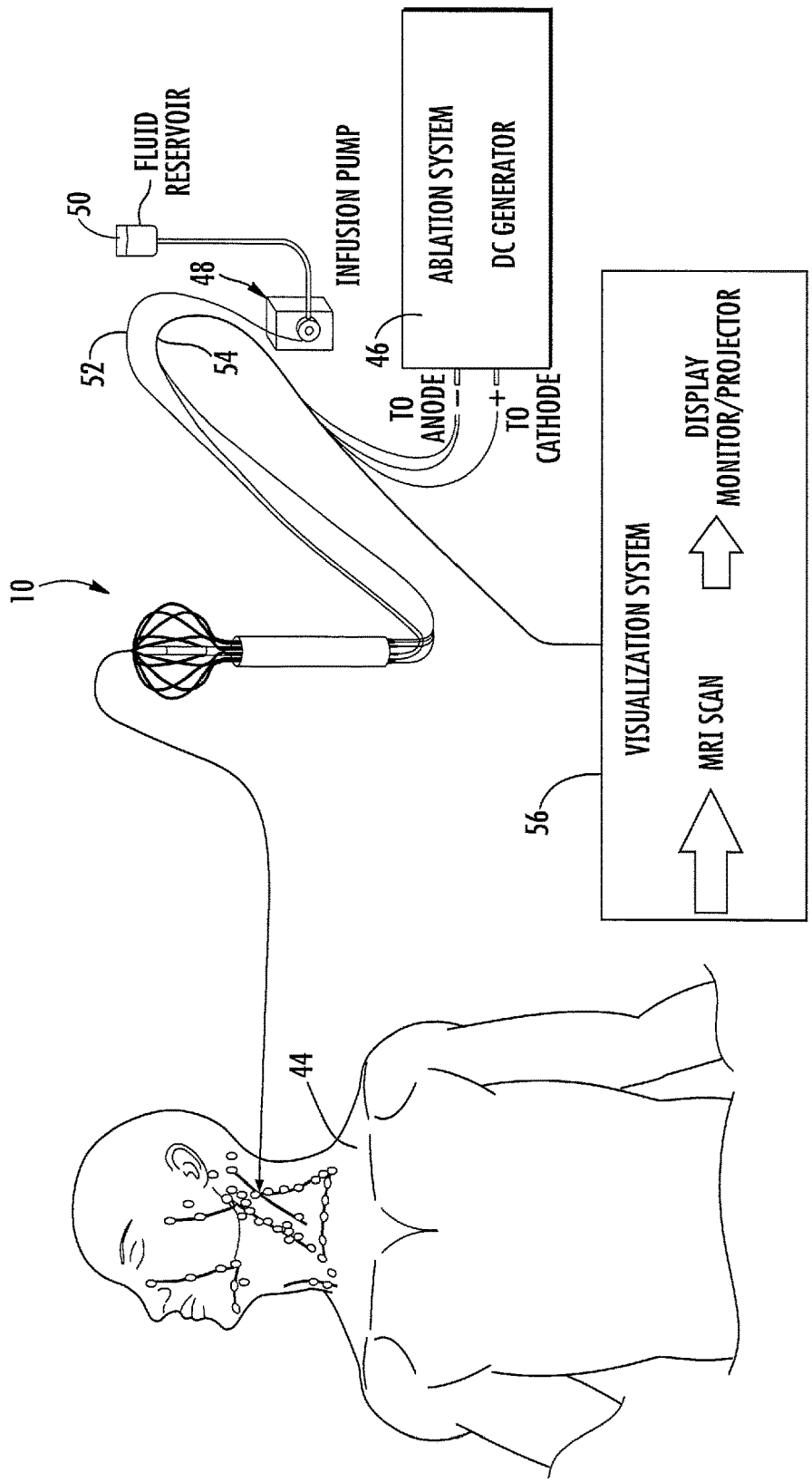
Figure 10:
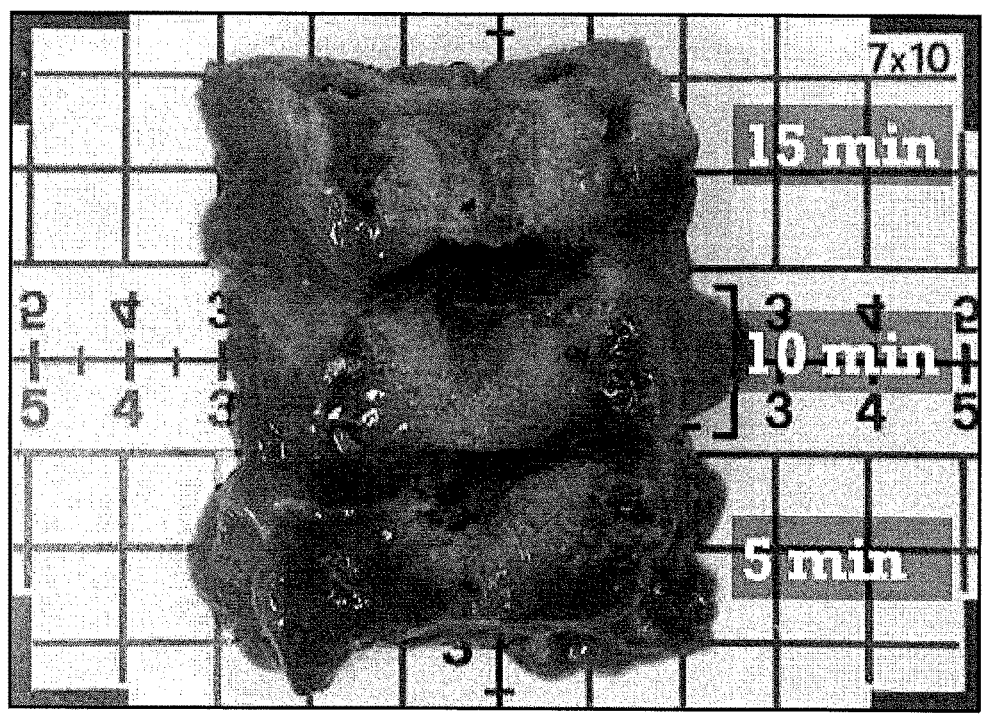

FIGS. 2AA-2GG illustrate different anode configurations for a coaxial ablation probe according to an embodiment of the subject matter described herein;

FIGS. 2HH-2JJ illustrate different configurations of a cathode cage for a coaxial ablation probe according to an embodiment of the subject matter described herein;

FIG. 3 is a schematic diagram illustrating a system for using a coaxial ablation probe to treat a patient's liver according to an embodiment of the subject matter described herein;

FIG. 4 is a flow chart illustrating an exemplary process for treating a patient using a coaxial ablation probe according to an embodiment of the subject matter described herein;

FIGS. 5A-5D illustrate the use of a coaxial ablation probe according to an embodiment of the subject matter described herein to treat a liver tumor;

FIG. 6A illustrates various ablation targets in a human liver for a coaxial ablation probe according to an embodiment of the subject matter described herein;

FIG. 6B is an image of a liver showing an ablated region near the gall bladder 72 without damage to gall bladder;

FIG. 7 is a diagram illustrating lymph nodes as potential ablation targets for a coaxial ablation probe according to an embodiment of the subject matter described herein;

FIGS. 8A-8E illustrate the use of a coaxial ablation probe according to an embodiment of the subject matter described herein to ablate a lymph node;

FIGS. 9A and 9B illustrate, respectively, lymph nodes of the head and neck and the use of an ablation system as described herein to ablate tumors in lymph nodes of the head and neck;

FIG. 10 is an image of an ex vivo bovine liver illustrating the results of ablation at different times. Serial ablation of 3 cm diameter, 2 cm thick ex vivo bovine liver at 5, 10, and 15 minutes demonstrate complete ablation by 15 minutes (32 V, 1.2-1.8 A). Notice the central zone of coagulation about the anode and peripheral liquefaction about the cathodes.

Figure 11A:
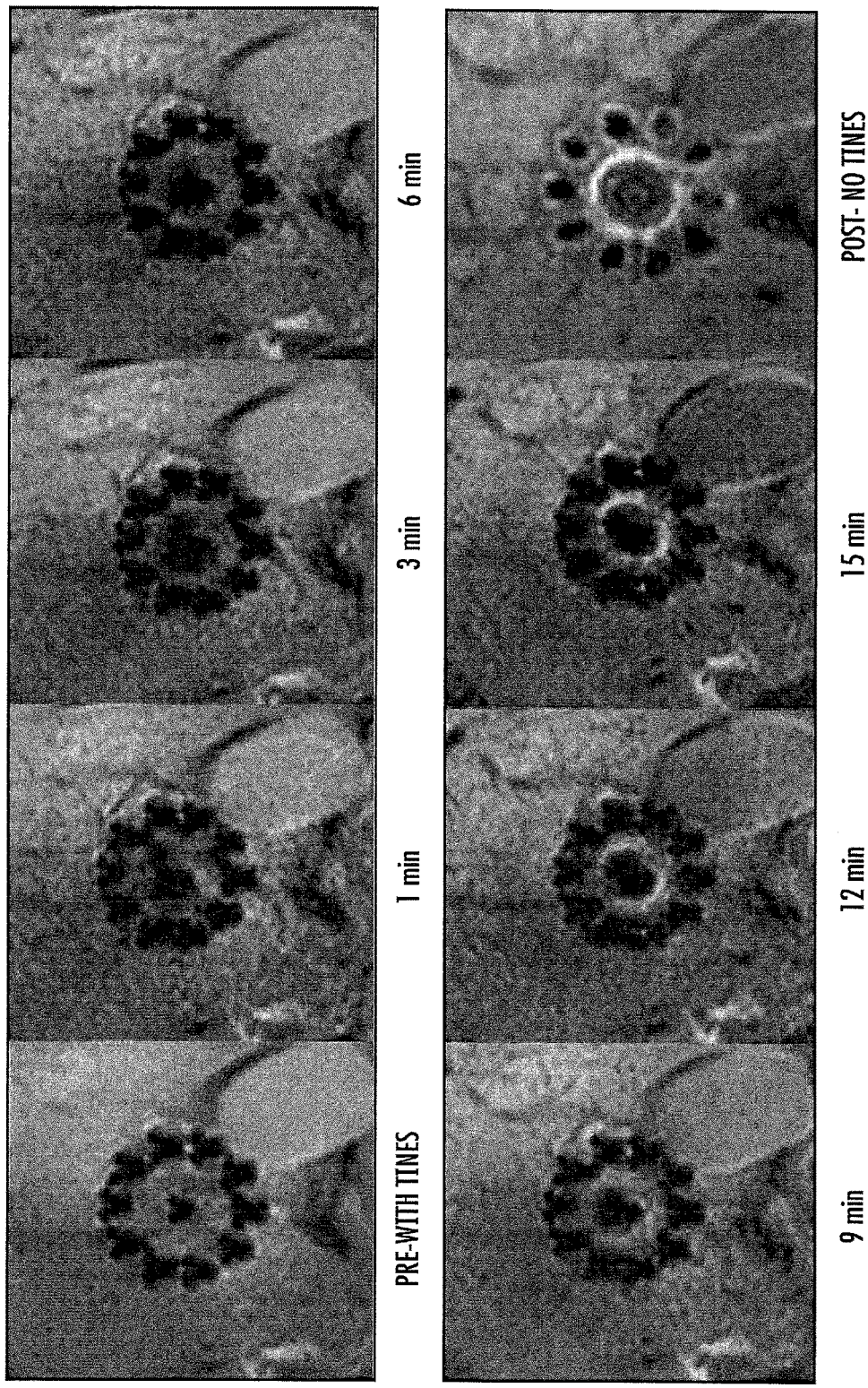

FIG. 11A illustrates real-time MRI monitoring of ablation treatment: In situ ablation progress was monitored using VIBE T1 sequences (TR/TE 5.0/2.2 ms, FA 15°, FOV 200 mm; Matrix 196×320; slice thickness 3 mm) along the short axis of the cathode cage. Sequences were performed before, during (3 minute intervals), and after ablation with the struts removed. In this example of a 3 cm ablation zone, T1 hypointense signal was seen to propagate circumferentially from the central anode towards the cathode with a leading edge of T1 hyperintense signal. Similar changes were seen at the cathode struts. Complete ablation was achieved when the signal changes coalesce.

Figure 11B:

FIG. 11B illustrates gross pathology correlation: On the left, a post-ablation TSE-T2 (TR/TE 5400/96 ms) image demonstrated T2 hypointense signal representing the ablation zone. Central T2 hyperintense signal about the anode represented hemorrhagic necrosis and the T2 hyperintense signal about the cathodes represented liquefactive necrosis. These MRI findings correspond to the changes seen on gross pathology.

Figure 11C:
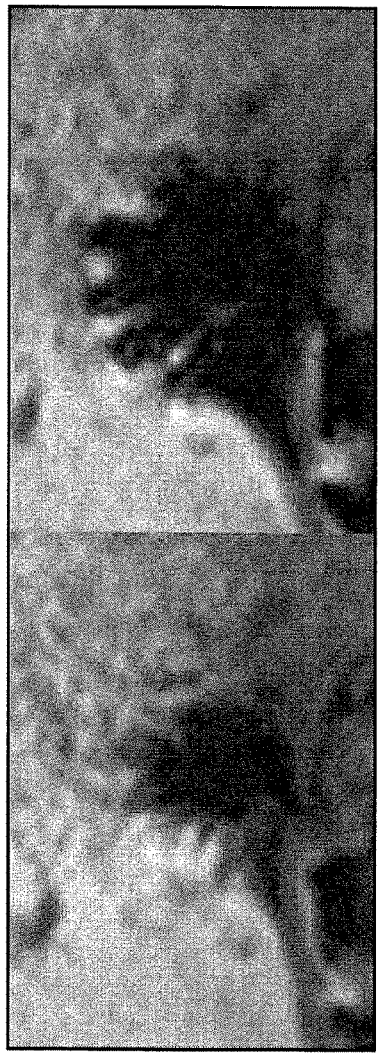

FIG. 11C illustrates results from testing of a coaxial ablation: In situ testing of the coaxial ablation probe using VIBE T1 along the short axis demonstrated a 2 cm ablation zone (left image) after 15 minutes (32 V, 0.3-0.9 A). Subsequently the struts in the 10:00 to 2:00 positions were manually adjusted to increase the radius by 1 cm and direct ablation towards the hepatic parenchyma (right image); ablation was performed for 6 additional minutes (32 V, 0.3-0.6 A).

6. DETAILED DESCRIPTION

The presently disclosed subject matter relates to novel devices and methods for performing and real-time monitoring of EChT. EChT is a percutaneous ablation technique utilizing direct current (DC) electricity to create toxic products to destroy abnormal tissue. The presently disclosed subject matter also relates to a coaxial ablation probe for EChT and/or other ablation techniques, including thermal ablation and irreversible electroporation.

6.1 Definitions

Unless otherwise defined, all technical and scientific terms used herein have the same meanings as commonly understood by one of ordinary skill in the art to which this invention belongs. Although methods and materials similar or equivalent to those described herein can be used in the practice or testing of the present invention, suitable methods and materials are described below, An "individual," "patient" or "subject," as used interchangeably herein, can be a human or non-human animal. Non-limiting examples of non-human animal subjects include non-human primates, dogs, cats, mice, rats, guinea pigs, rabbits, pigs, fowl, horses, cows, goats, sheep and cetaceans.

"Thermal ablation," as used herein, relates to percutaneous thermal tumor ablation techniques (radiofrequency, microwave, cryoablation, laser interstitial and high-intensity focused ultrasound), which have become accepted as an alternative to surgery (11, 25-30). For example, the curative potential of percutaneous ablation has been recognized by the Barcelona Clinic Liver Cancer (BCLC) group, which asserts that radiofrequency ablation of very small hepatocellular carcinomas (HCCs) is equivalent to surgical resection in terms of overall survival. However, the BCLC group has also demonstrated the major limitation of current ablation techniques is the higher rate of local recurrence compared to surgical resection (31). The higher risk of local recurrence results from inability to completely ablate the target tumor. The major drawbacks of current ablation technology include lack of real-time monitoring with standard imaging modalities, wide zones of transition between treated and untreated tissue, risk of non-target tissue damage, and heat sink effects in perivascular regions (1-11).

"Irreversible electroporation" (IRE), as used herein, relates to techniques wherein up to 45 A and 3,000 V in the form of micropulses are administered through percutaneously placed electrodes resulting in irreversible damage to cell membranes As a non-thermal ablation technique, IRE offers several advantages over traditional thermal techniques such as the ability to ablate lesions near large blood vessels. However, IRE has multiple limitations that has impaired the widespread adoption of this technology (51, 52). Similar to thermal ablation modalities, IRE produces a central ablation zone with surrounding penumbra of tissue damage and it is difficult to accurately assess treatment response on follow-up imaging (52). IRE is theoretically compatible with MRI but the wide zone of transition as well as the brief treatment time impedes accurate real-time MRI monitoring (52). Lastly, and perhaps the most significant shortcoming of IRE, is the requirements for general anesthesia and complete muscle paralysis to safely perform this technique (44, 48, 51).

"EChT," as used herein, relates to electrochemical treatment—an ablation technique that uses direct current (DC) to generate toxic species at the surface of electrodes and cause pH-mediated cell death. The main electrochemical reactions at the anode are the decomposition of water and oxidation of chloride ions resulting in free hydrogen ions, chlorine gas, and a strongly acidic environment resulting in coagulative necrosis (32):

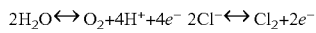
$$2H_2O \leftrightarrow O_2+4H^++4e^- \quad 2Cl^- \leftrightarrow Cl_2+2e^-$$

At the cathode, the main reaction is the decomposition of water into hydroxyl ions, hydrogen gas, and a strongly alkaline environment resulting in liquefactive necrosis (32):

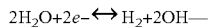
$$2H_2O+2e- \leftrightarrow H_2+2OH—$$

These species penetrate into the surrounding tissues predominately by diffusion and secondarily by electrically driven migration. Histologic examination of EChT demonstrates a sharply demarcated transition between necrotic and normal tissue with no damage to large vessels or extension of necrosis beyond an organ's capsule (13, 15-18). The most important treatment parameters that determine the rate and size of the EChT ablation zone are the electrode surface area, local ionic content and the total charge—a product of current and exposure time (12-24, 33-42). The total charge was found to have a linear relationship to the ablation rate and volume (15, 21, 22, 33, 36, 43). EChT has been performed on tens of thousands of patients to treat lung, GI, and soft tissue tumors with minimal local discomfort and without any reported serious side effects or deaths related to treatment (13-15, 17, 18, 37, 41).

The term "magnetic resonance" or "MR", as used herein, is a diagnostic and imaging modality that is capable of providing a three-dimensional map, or image of tissues of interest. In magnetic resonance imaging (MRI), a target tissue is exposed to a strong, substantially constant static magnetic field. The static magnetic field causes the spin vectors of certain atomic nuclei within the tissue to randomly rotate or "precess" around an axis parallel to the direction of the static magnetic field. Radio frequency excitation energy is then applied to the tissue and this energy causes the nuclei to "precess" in phase and in an excited state. As the precessing atomic nuclei relax, weak radio frequency signals are emitted; such radio frequency signals are referred to herein as magnetic resonance signals. In this way, magnetic resonance offers the ability to produce three-dimensional tissue images without the ionizing radiation associated with other imaging modalities. Magnetic resonance also provides real-time images with excellent tissue contrast; thus, entire target tissues can be quickly and efficiently visualized and healthy, viable, tissue can be differentiated from abnormal tissue.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to +/−20%, preferably up to +/−10%, more preferably up to +/−5%, and more preferably still up to +/−1% of a given value. Alternatively, particularly with respect to biological systems or processes, the term can mean within an order of magnitude, preferably within 5-fold, and more preferably within 2-fold, of a value.

6.2 Coaxial Ablation Probe

Figure 2B:
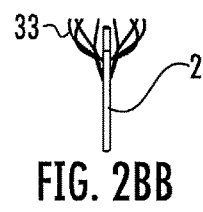
Figure 2C:
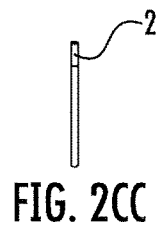

In certain embodiments, the coaxial ablation probe employed in the context of the methods disclosed herein will be a nested electrode device. In certain embodiments, the device will be a coaxial probe. In certain embodiments, a coaxial ablation probe 10 will comprise a cathode cage (see 1 in FIG. 2C) surrounding an anode (see 2 in FIG. 2C). In certain embodiments the anode 2 will be provided with its own insulating sheath (see 3 in FIG. 2C). In certain embodiments, the anode sheath 3 will be fixed to the apex of the cathode cage to provide stability and the ability to use manual traction to expand the cage. In certain embodiments, the electrode pair is loaded into an outer insulating catheter or sheath (see 4 in FIG. 2C). In certain embodiments, the anode sheath 3 will have configurations similar to the outer catheter or sheath (FIGS. 2E-2I). In certain embodiments, the compact coaxial ablation probe design will be contained within a catheter having an inner diameter from about 0.3 mm to about 3.0 cm and will allow for percutaneous insertion under MR guidance. In certain embodiments, the catheter will have an outer diameter from about 0.4 mm to about 3.5 cm. In certain embodiments, the compact design and sharp tip of the un-deployed probe (see FIG. 2A) allows for easy percutaneous insertion. In certain embodiments, probe 10, once inserted, can be opened to varying diameters. The dimensions and operational size range of probe 10 can be scaled according to a particular application. For example, if probe 10 is designed for ablating liver tumors, cathode cage 1 may have a diameter of about 2 cm upon insertion and may be expanded to a diameter of about 5 cm after expansion of struts 12 during treatment. If probe 10 is designed for ablating lymph node, cathode cage 1 may have a diameter of about 2 mm upon insertion and may be expandable to about 1 cm after expansion during treatment. FIG. 2B illustrates expansion of cathode cage 1 after unsheathing. FIG. 2C illustrates expansion of cathode cage 1 to a larger diameter than that in FIG. 2B after tissue ablation.

As illustrated in FIG. 2A, probe 10 is in the un-deployed state where individual struts 12 are confined by outer sheath 4 to a generally cylindrical configuration. Individual struts 12 are resiliently biased against the inner wall of outer sheath 4. When outer sheath 4 is moved axially away from probe tip 14, struts 12 expand radially outwardly to form, in one embodiment, a generally spherical shape. In another embodiment, the shape defined by the volume surrounded by struts 12 may be any desired shape, such as a sphere, an ellipsoid, a non-curvilinear closed shape, or an open shape, as will be described in detail below. When energized by a power source, the volume surrounded by struts 12 defines a treatment region.

Figure 2D:
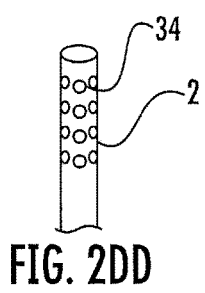
Figure 2E:
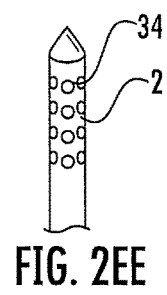
Figure 2F:
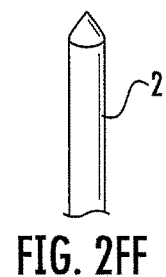
Figure 2G:
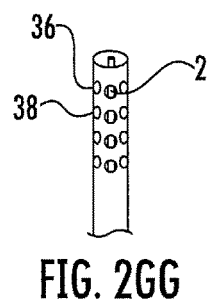
Figure 2H:
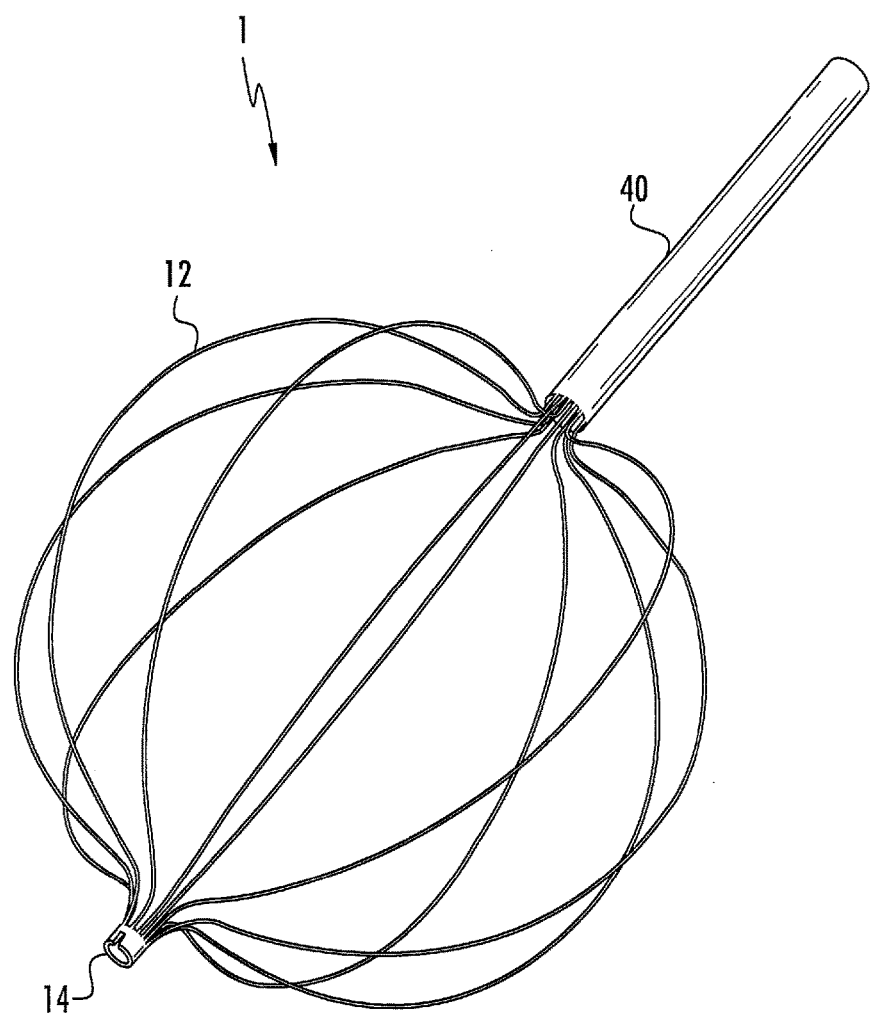
Figure 2I:
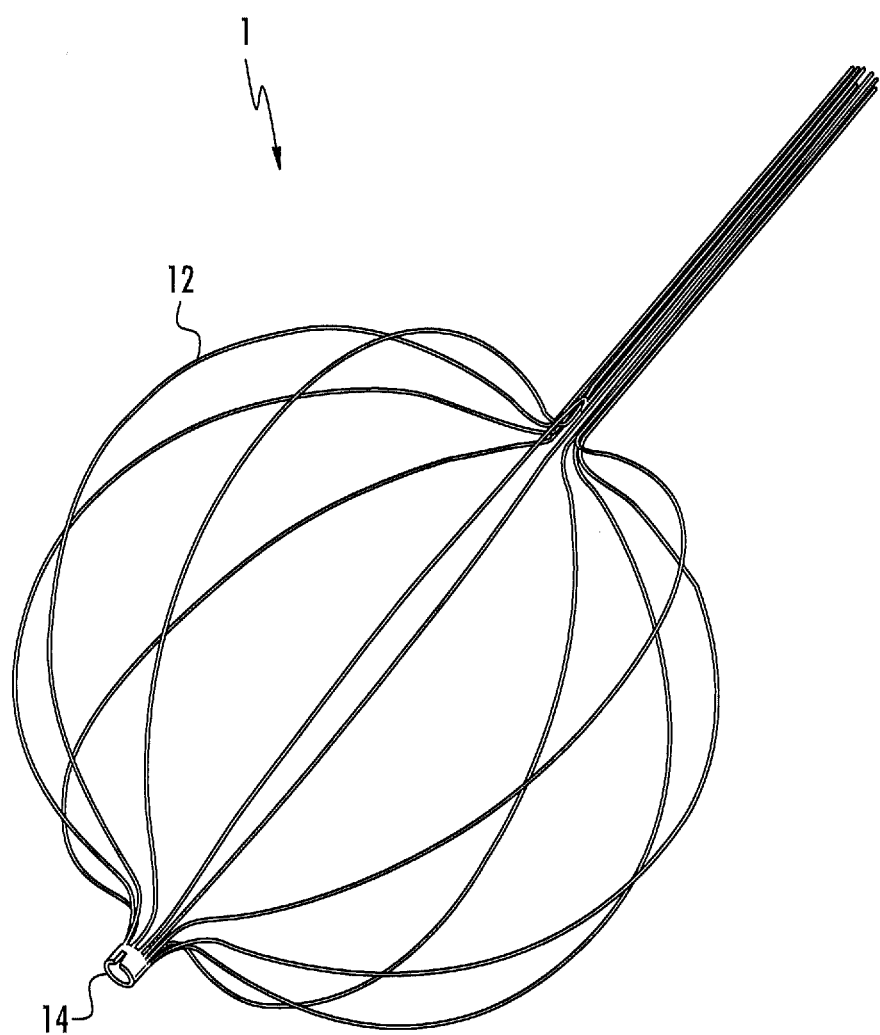
Figure 2J:
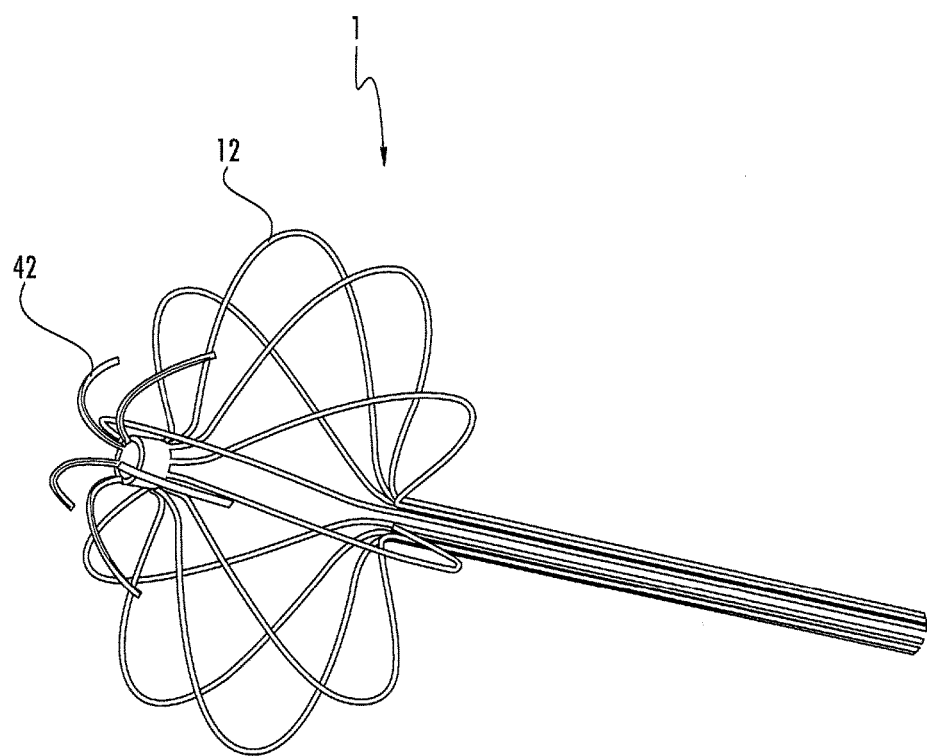

As illustrated in FIG. 2D, if it is desirable to change the shape of the volume surrounded by struts 12 to change the treatment region, struts 12 can be individually moved to change the shape of the volume surrounded by struts 12. In one embodiment, each strut 12 can be individually extended or retracted by pushing axially towards or away from the cathode tip 14 on each individual strut 12. In another embodiment, as will be described in more detail below, outer sheath 4 may include actuators for individually moving each strut 12.

In one embodiment, outer sheath 4 may include axial guides to prevent twisting of struts 12. FIGS. 2E-2G illustrate one embodiment of outer sheath 4 that includes axially extending channels or guides to prevent twisting of struts 12. Referring to FIG. 2E, outer sheath 4, when viewed from an axial direction, includes channels 16 formed in the inner diameter of outer sheath 4. Channels 16 may extend axially the entire length of the outer sheath 4. As illustrated in FIG. 2G, struts 12 may rest in each channel 16.

In FIG. 2G, channels 16 are open on one side. In another embodiment, each channel 16 may be a cylindrical channel that is closed, as illustrated in FIGS. 2H and 2I. In FIG. 2H, each channel 16 comprises a cylindrical cavity extending axially through outer sheath 4. Each strut 12 may reside in one of channels 16 to prevent or reduce twisting of struts 12.

As stated above, probe 10 may allow struts 12 to be individually moved in an axial direction to change the shape of the volume defined by struts 12. FIG. 2J illustrates that embodiment where outer sheath 4 includes actuators 18 that reside in grooves 20 formed in outer sheath 4. Each actuator 18 may be attached to one of struts 12. When an actuator 18 slides within a groove 20, the respective strut 12 bends either radially outwards or inwards, depending on the direction of movement of the actuator 18. Each actuator 18 may have a generally hyperbolic profile, if viewed from the side as illustrated in FIG. 2K. The outward facing surface 22 of each actuator 18 may include ridges or grooves to facilitate gripping. As illustrated in the side view in FIG. 2L, each actuator 18 may further include a strut holder 24 that extends into each groove 20 and holds its respective strut 12. As illustrated in FIG. 2M, strut holder 24 may include a central aperture 26 through which a strut 12 passes. As illustrated by the magnified view in FIG. 2J, each groove 20 may include teeth 21 that allow locking of an actuator 18 in a position corresponding to a desired degree of radial expansion of its respective strut 12.

Cathode cage 1 may have any one of a number of different shapes or configurations. FIGS. 2M-2Q illustrate different configurations of cathode cage 1 according to an embodiment of the subject matter described herein. As illustrated in FIG. 2N, cathode cage 1 defines a closed volume that is generally ellipsoidal in shape. As illustrated in FIG. 2O, cathode cage 1 defines an open volume that has a tulip-like shape. As illustrated in FIG. 2P, cathode cage 1 includes cross-shaped support struts 28 extending laterally between struts 12 to provide structural support for cathode cage 1. In FIG. 2Q, linear support struts 30 extend between adjacent struts 12.

According to another aspect of the subject matter described herein, struts 12 may include any of a plurality of different radial cross sections. FIGS. 2R-2V illustrate different radial cross sections and configurations for struts 12. As illustrated in FIG. 2R, an individual strut 12 comprises a hollow cylindrical tube with apertures 32 to allow fluid flow from within strut 12 to the volume surrounded by cathode cage 1. In one example, a fluid may be pumped through apertures 32 to increase the rate of the chemical reaction occurring within the volume defined by cathode cage 1.

Any suitable fluid may be pumped through apertures in cathode cage 1 or in anode 2 without departing from the scope of the subject matter described herein. Examples of fluids that may be pumped through apertures 32 in cathode cage 1 or in apertures in anode 2 (described below) include water, medication, chemotherapy, contrast agents, or ablation-assisting fluids, including electrolytes, such as a saline solution. In addition, apertures in cathode cage 1 and/or in anode 2 may be used to withdraw fluid and ablated tissue from the treatment region defined by cathode cage 1.

In another embodiment, as illustrated in FIG. 2S, a strut 12 may have a triangular profile where one vertex of the triangle extends radially outward. Such a profile may facilitate cutting into tissue by struts 12.

In yet another example, as illustrated in FIG. 2T, each strut 12 may have a circular profile either with or without apertures.

FIG. 2U illustrates another example where each strut 12 has a blade-like radial profile. In such a profile, the sharpened point of the blade extends radially outward to facilitate cutting of tissue.

In yet another embodiment, as illustrated in FIG. 2V, each strut 12 may have a rectangular profile.

As cathode cage 1 may include different configurations, anode 2 may also include different configurations. FIGS. 2AA-2GG illustrate different configurations of anode 2. In FIG. 2AA, anode 2 includes individual struts 33 that form a closed cage, similar to cathode cage 1 illustrated in FIG. 2B. In such an embodiment, the volume defined by anode 2 may be smaller in diameter than that defined by cathode cage 1. As illustrated in FIG. 2BB, anode 2 includes individual struts 33 that define an open cage. In FIG. 2CC, anode 2 comprises a wire with a generally cylindrical and solid radial cross section. In FIG. 2DD, anode 2 comprises a hollow cylindrical tube with apertures 34 formed in the tube, with or without a closed tip, to facilitate pumping of a fluid, such as an electrolyte solution, through apertures 34. In FIG. 2EE, anode 2 includes a needle-like closed tip with apertures 34 to facilitate fluid flow from the interior of anode 2 into the treatment volume or from the treatment volume into the interior of anode 2. In FIG. 2FF, anode 2 forms a needle-like structure with or without apertures 34. In FIG. 2GG, anode 2 comprises a wire surrounded by an outer insulating tube, with or without a closed tip 36. Apertures 38 may be formed in tube 36 to allow fluid flow from the interior of tube 36 into the treatment volume or from the treatment volume into the interior of tube 36. It should also be noted that anode configurations in FIGS. 2CC-2GG may be used utilized in singularity or plurality. It should also be noted that anode 2 may have any of the cross sections illustrated in FIGS. 2R-2V. It should also be noted that anode insulting sheaths 3 may have similar constructions as illustrated in FIGS. 2E-2I for different anode configurations and plurality.

FIGS. 2HH-2JJ illustrate different embodiments of cathode cage 1. In FIG. 2HH, cathode cage 1 is formed by cutting axial grooves in a tube. In such an embodiment, struts 12 may not be adjustable. As illustrated in FIG. 2HH, cathode cage 1 includes a lower portion 40 that is a generally cylindrical tube and an upper portion formed by struts 12. In the illustrated example, cathode tip 14 comprises an uncut portion of the uncut tube that mechanically joins struts 12 together at the apex of cage 1. In the example illustrated in FIG. 2HH, probe tip 14 may allow anode 2 to pass through its inner diameter and puncture tissue. In an alternate embodiment, as illustrated in FIG. 2A, cathode tip 14 may include a point or conical structure to facilitate puncturing of tissue.

In FIG. 2II, cathode cage 1 includes struts 12 that are individually adjustable. As such, each strut 12 is axially separate from its adjacent times throughout the entire axial length of each strut 12.

FIG. 2JJ illustrates another embodiment of cage 1 where struts 12 form a tissue anchor 42 at the apex of cage 1. Tissue anchor 42 is formed by bending the end of each strut 12 in an almost 180° bend to form a hook-like structure. In operation, tissue anchor 42 may anchor into tissue being treated to provide better stability of probe 10.

FIG. 3 is a diagram illustrating an exemplary system for using probe 10 for ablating liver tumors according to an embodiment of the subject matter described herein. Referring to FIG. 3, probe 10 is designed to be used by inserting probe 10 into the patient 44 percutaneously and into the tissue being treated. A DC generator 46 creates a DC potential across anode 2 and cathode cage 1. An infusion pump 48 may pump fluid from a fluid reservoir 50 into the tissue volume through apertures in struts 12 or in anode 2 as described above. DC generator 46 may be connected to anode 2 via anode wire 52. DC generator 46 may be connected to each cathode strut via cathode strut wires 54. A visualization system 56 may include surface MRI coils worn by the patient to receive the MRI signal generated in response to tissue excitation by MRI transmit coils. Because probe 10 is compact in size, probe 10 can be used to operate on a patient between the surface MRI coils and when the patient is within the bore defined by the MRI transmit coils.

During electrochemical treatment, the interventional radiologist may monitor the progress of the ablation via a display which displays in real time or in near real time a magnetic resonance image of the tissue volume being treated and the surrounding tissue. The display may be part of visualization system 56 and may be a monitor, a projector, or a head mounted display. Because surface coils are worn on the surface of the patient's body, high resolution images are available.

FIG. 4 is a flow chart illustrating an exemplary process for treating patients using probe 10 according to an embodiment of the subject matter described herein. Referring to FIG. 4, in step 100, an ablation target is identified. The ablation target may be a liver tumor, a lymph node, or any other tissue for which ablation treatment is desired. In step 102, probe 10 is inserted into the patient centered on the target identified in step 100. Probe 10 may have any of the configurations described herein. Probe 10 may be inserted into the tissue to be treated, for example, into the patient's liver or other organ.

In step 104, cathode cage 1 is unsheathed to a desired diameter. Unsheathing cathode cage 1 may include sliding sheath 4 axially away from apex 14 of probe 10 to allow struts 12 to expand to their pre-treatment diameter. In step 106, a DC bias is applied to probe 10. The DC bias is applied between anode 2 and cathode cage 1. The DC bias causes an electrochemical reaction (described above) in the treatment volume, as defined by volume enclosed within the cathode cage struts 12, which ablates tissue within the treatment volume with minimal effect on tissue outside of the treatment volume. In step 108, a fluid is pumped into the treatment volume. The fluid may be any of the fluids described above, for example, to enhance the treatment or to allow better monitoring of treatment progress. In step 110, the treatment progress and probe expansion are monitored. Monitoring the treatment progress and probe expansion may include viewing real time images of the treatment volume and the cathode cage as shown on the display coupled to the surface MRI coils. In step 112, the probe and/or individual struts may be repositioned to change the treatment volume. Steps 110 and 112 may be repeated until the desired treatment has been achieved. For example, if the treatment is the ablation of a tumor, the probe may be repositioned until the entire tumor and desired margins around the tumor have been ablated. In step 114, the loss of normal signal on the MRI monitoring sequence is identified. The normal signal may be the signal that indicates the tissue within the treatment volume. In step 116, the probe is withdrawn and the tissue tract may be ablated with thermal energy or electrochemical ablation to reduce bleeding, if desired. Enlarging the cage or withdrawing the probe may include adjusting actuators 18 to return each strut 12 to the minimum of the adjustment range defined by each actuator 18, sheathing cathode cage 1 to decrease the diameter of cathode cage 1 to its insertion diameter and then withdrawing probe 10 through the same tract used for insertion.

In certain embodiments cathode cage 1 will include a plurality of struts 12. For example, but not by way of limitation, the number of struts 12 can range from 1 to about 100. In certain embodiments, the number of struts 12 will be from about 2 to about 25 struts. In certain embodiments the number of struts 12 will be from about 4 to about 16 struts 12. In certain embodiments the number struts 12 will be 4, 5, 6, 7, 8, 9, 10, 11, 12, 13, 14, or 15. Struts 12 may have any of the configurations described above with respect to FIGS. 2N-2V In certain embodiments, cathode cage 1 will be comprised of wire having a diameter from about 0.1 mm to about 10 mm. Struts 12 may be formed of any suitable conductive material that has sufficient flexibility to allow expansion and contraction to achieve a desired treatment volume. Examples of suitable materials for struts 12 include metals, such as copper, gold, or platinum; metal alloys, such as nickel-titanium alloys; or conductive plastics. One example of a nickel-titanium alloy suitable for use to form struts 12 is nitinol.

Similar to struts 12, anode 2 may also be formed of any suitable conductive material, such as any of the materials listed above for struts 12. If anode 2 needs to have a flexible configuration, such as that illustrated in FIGS. 2AA and 2BB, anode 2 may also be comprised of a flexible metallic material. If flexibility is not a requirement of anode 2, more rigid materials can be used than those used for struts 12.

Anode 2 may have any of the configurations described above with respect to FIGS. 2AA-2GG. In addition, the number of anodes or number of anode members may vary. For example, but not by way of limitation, the number of anodes or anode members can range from 1 to about 100. In certain embodiments, the number of anodes or anode members will be from about 2 to about 25. In certain embodiments the number of anodes or anode members will be from about 4 to about 16. In certain embodiments the number anodes or anode members will be 4, 5, 6, 7, 8, 9, 10, 11, 12, 13, 14, or 15. In certain embodiments, the anode will be comprised of wire having a diameter from about 0.1 mm to about 10 mm.

In certain embodiments, cathode cage 1 will be freely mobile within the outer sheath and adjustable in diameter from about 0.05 to about 10 cm depending on the amount of unsheathing. Sheath 4 may confine cathode cage 1 to its minimum diameter before unsheathing. Sheath 4 may be cylindrical and uniform in diameter. Alternatively, sheath 4 may be tapered or conical in shape with the smaller diameter at the insertion end and a larger diameter at the opposite end for ergonomic purposes. Furthermore, as stated above, each strut 12 of cathode cage 1 may be able to move independently to allow for more versatile contouring. In certain embodiments, the arrangement of anode 2 and cathode cage 1 will permit enough space to inject any fluid into the treatment volume or withdraw material from the treatment volume, as described above.

EChT has traditionally been performed with two or more platinum electrodes (21, 41, 43). Because electrochemically soluble metals will dissolve with anodic current, platinum has traditionally been used for EChT electrodes (32). However, because the cathode is protected against electrochemical dissolution by the cathodic current, it is possible to use metals with mild solubility, such as nitinol, as the cathode for EChT (53). Thus, in certain embodiments, the cathode cage of the coaxial ablation probes described herein can be made of nitinol or any of the other materials described above.

Nitinol has seen increased utilization for medical devices since the 1980s because of its shape memory and MRI compatibility (54-57). Nitinol's shape memory results from transformation of the metal's atomic structure from a cubic crystal configuration at high temperatures (austenite) to a monoclinic crystal at low temperatures (martensite) (58, 59). These transitions are reproducible when the metal is heated to body temperature or if an electric current is passed through the wire (60). Overall, these properties allow for construction of a nitinol cathode cage that can be compacted around a platinum electrode for percutaneous delivery as a catheter. In certain embodiments, the catheter can have an inner diameter of about 2 mm to about 1 cm.

Once probe 10 is positioned and the cathode unsheathed, the heat from physiologic temperatures, electric current from the DC generator, and liquefactive necrosis created by cathode cage 1 will allow cage 1 to return to its shape-formed geometry. The shape-formed geometry may be any of the geometries described above for cathode cage 1. The shape-formed geometry refers to the geometry formed by cathode cage 1 through self expansion after being unsheathed. In certain embodiments, such geometry is defined at manufacturing time when struts 12 are heated held in position to form the desired geometry, and then cooled so that the geometry will be maintained. This principal is similar to the design and function of nitinol self-expanding stents. In certain embodiments, manual traction applied to the probe can augment the re-expansion process.

In certain embodiments, the nested electrode devices (coaxial ablation probe) described herein can be controlled via a steering and deployment system. In certain embodiments, such steering and deployment system can be operably linked to the nested electrode device. For example, but not by way of limitation, a sleeve of similar or different diameter to the sheath (see (4) in FIG. 2A) can be used as housing for steering and deployment system. In certain embodiments, the steering and deployment system will allow for independent control of the struts of the cathode cage, for example, by way of independently controllable pistons. Exemplary steering and deployment systems can be found in U.S. Pat. Nos. 6,066,125, 8,548,567, U.S. Patent Application Publication No. 20110144576, and PCT Patent Publication WO 2012177586.

6.3 Real-Time Monitoring of EChT for Treatment of Abnormal Tissue

The presently disclosed subject matter provides for devices and methods for treating abnormal tissue using minimally invasive techniques and real-time monitoring of the administration of such treatments. One such minimally invasive technique, EChT, has traditionally been performed using two or more platinum electrodes, which can be cumbersome, slow, difficult to contour, and lack adequate methods for monitoring ablation progress. As described above, the techniques of the present application involve, in certain embodiments, the use of novel ablation devices comprising a coaxial ablation probe with a size- and shape-adjustable nitinol cathode cage encasing a platinum anode. The ability to shape form and adjust individual components of the nitinol cage allows for specific contouring to a target lesion's geometry. Nitinol's MR compatibility and the sharply demarcated EChT treatment margins allow for accurate real-time monitoring and adjustment of the ablation zone. Ablation sizes achieved using the devices and methods described herein will be dependent upon total charge delivered. In certain embodiments, the total charge will range from about 100 to about 1,000,000 Coulombs, depending on lesion size. A Coulomb is the unit for total charge and is defined as the charge transported by a constant current of one ampere in one second. In certain embodiments the total charge will range from about 100 to about 100,000 Coulombs/cm$^3$ at a direct current of about 0.1 to about 30 A. In certain embodiments, this charge will be delivered continuously rather than in pulses.

Advantages of the coaxial ablation probe and methods described herein over current thermal ablation techniques include, but are not limited to: the ability to achieve sharp demarcations between treated and untreated tissue; lowered risk of non-target injury to adjacent organs; little or no pain from the ablation; and immunity to heat sink effects from large vessels adjacent to the ablation target. Data disclosed herein, e.g., FIGS. 1A, 1B, 6B, 10, 11A, 11B, and 11C, demonstrate the sharply marginated EChT ablation zones correlates precisely to signal changes on magnetic resonance (MR) imaging. This offers a significant advantage over current ablation techniques as real-time monitoring of ablation can allow intra-procedural adjustments to ensure complete treatment of the target lesion.

Real-time monitoring of methods disclosed herein via magnetic resonance can be achieved using a variety of magnetic resonance imaging techniques. For example, but not by way of limitation, U.S. Pat. Nos. 5,647,361, 7,175,829, and 8,396,532 describe a variety of magnetic resonance imaging techniques that can find use with the compositions and methods disclosed herein. In certain embodiments, such real time monitoring allows for the characterization of the ablation operation during the course of the operation. This real-time information provides reliable indications of the characteristics (e.g. area, volume and/or depth) of the lesions created during ablation procedure, and thereby allows for intra-procedural adjustments.

In certain embodiments, the rate and size of ablation will be dependent upon the electrode surface area, total charge, and free ions in the treatment zone. Therefore, in certain embodiments, the rate of ablation can be enhanced and the ablation zone enlarged by making one or more of the following, non-limiting, adjustments: 1) expanding the nitinol cage diameter to increase surface area; 2) amplifying the current to increase total charge; and 3) injecting saline or other ionic fluid to augment free ions.

In certain embodiments, the methods disclosed herein will find use in the treatment of cancerous tumors, including, but not limited to hepatocellular carcinoma, hepatic metastases, other solid organ or soft tissue tumors, and metastatic lymph nodes. For example, but not by way of limitation, the curative potential of percutaneous ablation has been recognized by the Barcelona Clinic Liver Cancer (BCLC) group, which asserts that radiofrequency ablation of limited grade hepatocellular carcinomas (HCCs) up to 3 cm in size (and up to 3 nodules) is equivalent to surgical resection in terms of overall survival. However, the BCLC group conceded that the major limitation of current ablation techniques is the higher rate of local recurrence compared to surgical resection (31). This higher risk of local recurrence results from inability to completely ablate the target tumor in the treatment zone. Other major drawbacks of current ablation technology include wide zones of transition between treated and untreated tissue, risk of non-target tissue damage, heat sink effects in perivascular regions, and lack of real-time monitoring with standard imaging modalities (1-11). Implementation of the coaxial ablation probe and methods described herein, such as, but not limited to, the use of real-time magnetic resonance monitoring of electrochemical treatment administered via a coaxial ablation probe addresses the need identified in the art.

Although the coaxial ablation probes disclosed herein are primarily described in the context of the performance of EChT, these devices can also be used in the context of alternative ablation techniques. Such alternative ablation techniques include, but are not limited to: thermal ablation (where heat is transmitted to the treatment site via the metallic components of the coaxial ablation probe) and irreversible electroporation.

Figure 5A:
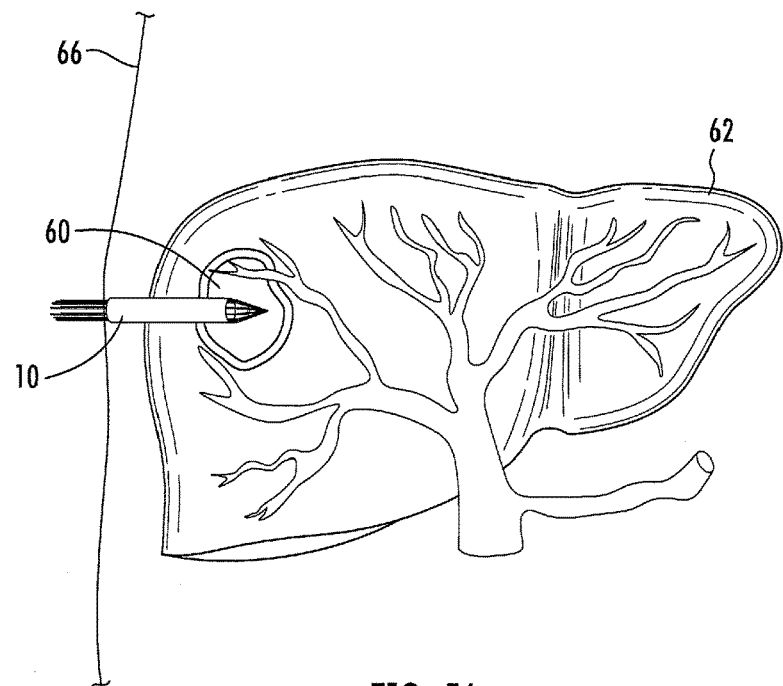

As stated above, probe 10 may be used to treat tumors in different parts of the human anatomy, including, but not limited to the liver, lymph nodes, or other solid organ tumors. FIGS. 5A-5D illustrate the use of probe 10 to treat a tumor in a human liver. In FIG. 5A, probe 10 is shown in its insertion state with struts 12 of cathode cage 1 undeployed or sheathed. Probe 10 is inserted into tumor 60 in a human liver 62. Probe 10 may be inserted an incision in the patient's skin 66.

Figure 5B:
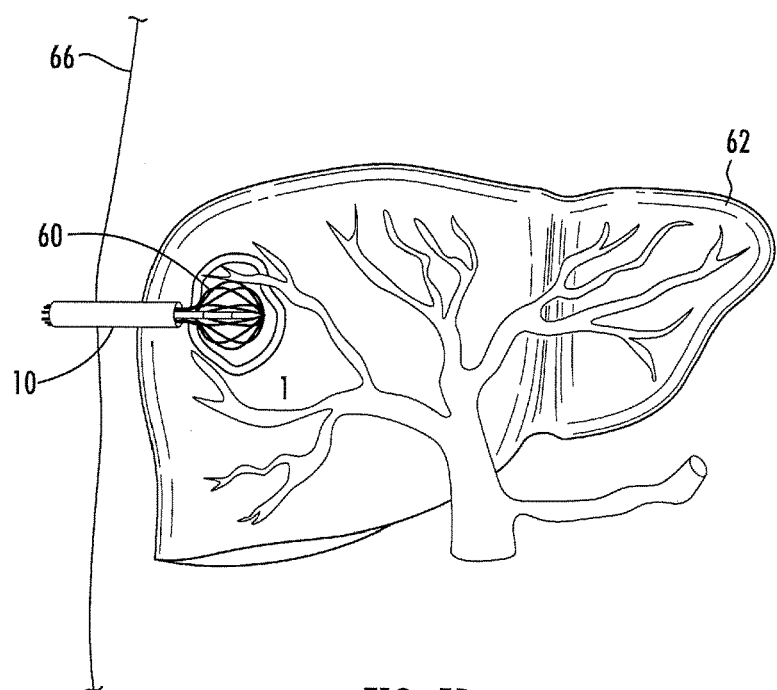

In FIG. 5B, cathode cage 1 is unsheathed. At this stage, treatment begins applying a DC voltage across cathode cage 1 and anode 2. Fluid may also be pumped into the treatment volume defined by cathode cage 1 through apertures in the cathode 1 or anode 2 as described above.

Figure 5C:
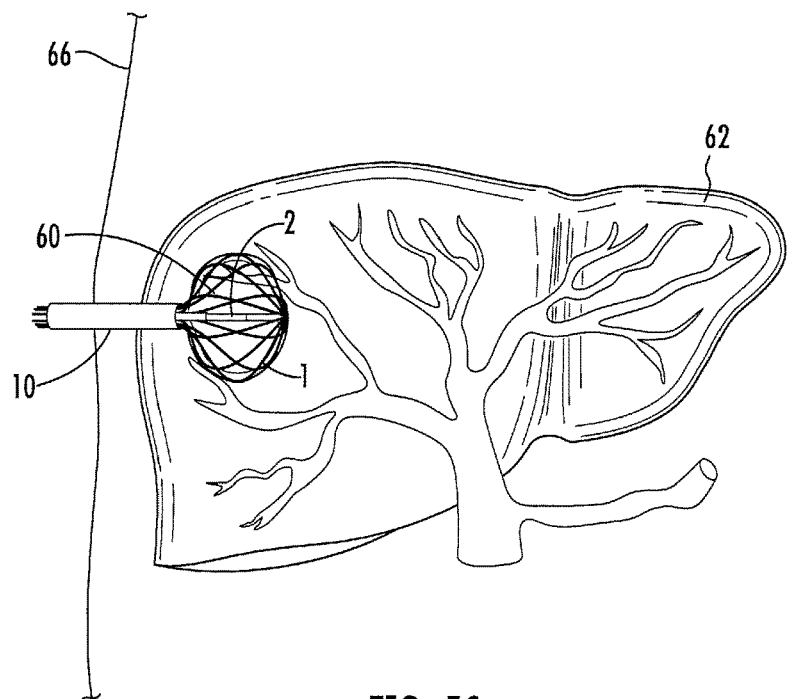
Figure 5D:
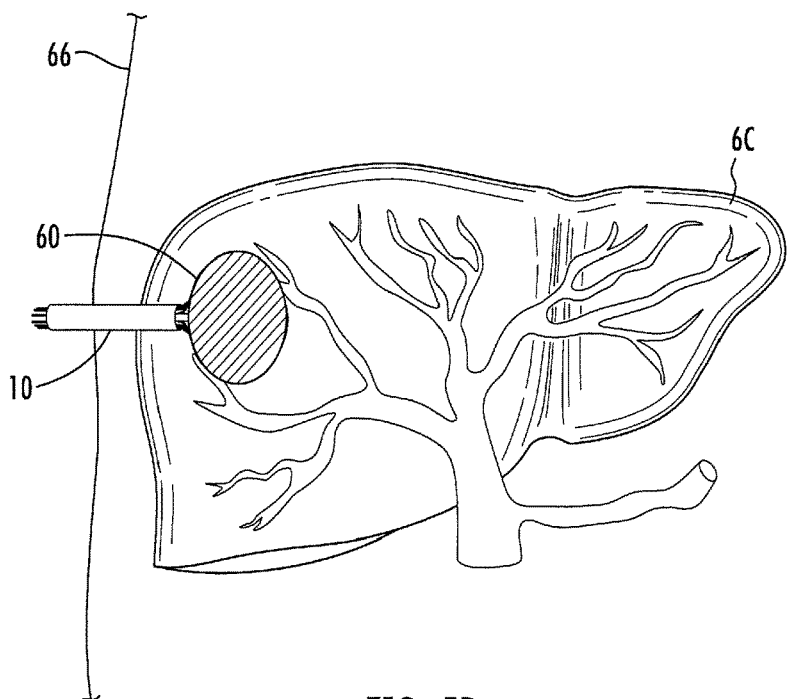

FIG. 5C illustrates further expansion of cathode cage 1 as treatment progresses. FIG. 5D illustrates full expansion of cathode cage 1 and complete ablation of tumor 60, indicated by the shaded region.

FIG. 6A illustrates ablation of different regions in the human liver. In FIG. 6A, A-D indicate possible ablation targets in the human liver 70. Ablation target A is adjacent to the gall bladder 72. Ablation target B is adjacent to a large blood vessel. Ablation target C is adjacent to the pancreas 74. Ablation target D conforms to the hepatic capsule adjacent to the superior vena cava 76.

FIG. 6B is an image of a liver after ablation. In FIG. 6B, liver 70 and gall bladder 72 are illustrated. The dark region in liver 70 adjacent to gall bladder 72 is the ablation region. The ablation region does not extend into gall bladder 72, illustrating the ability of probe 10 to ablate tissue adjacent to vital structures without damage to that vital structure.

Figure 8A:
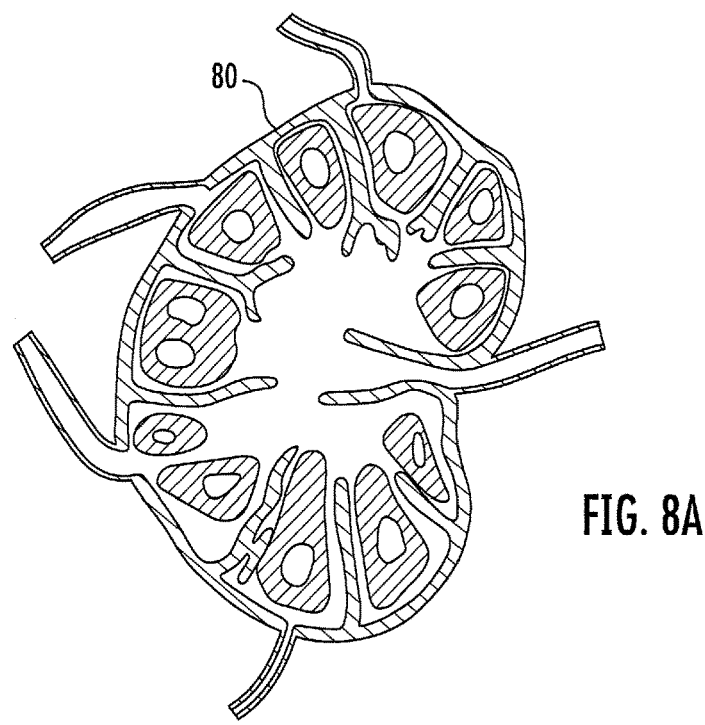
Figure 8B:
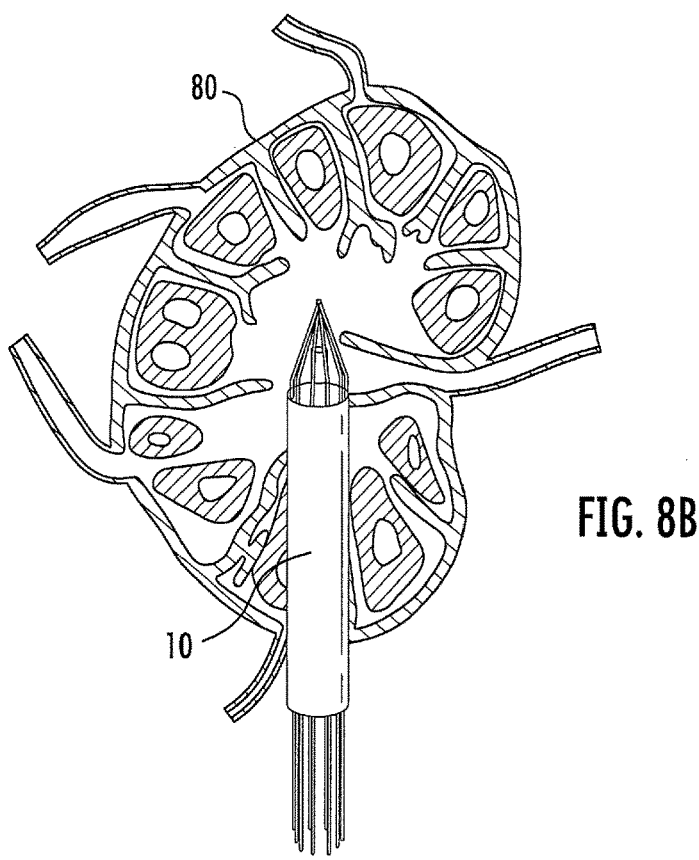
Figure 8C:
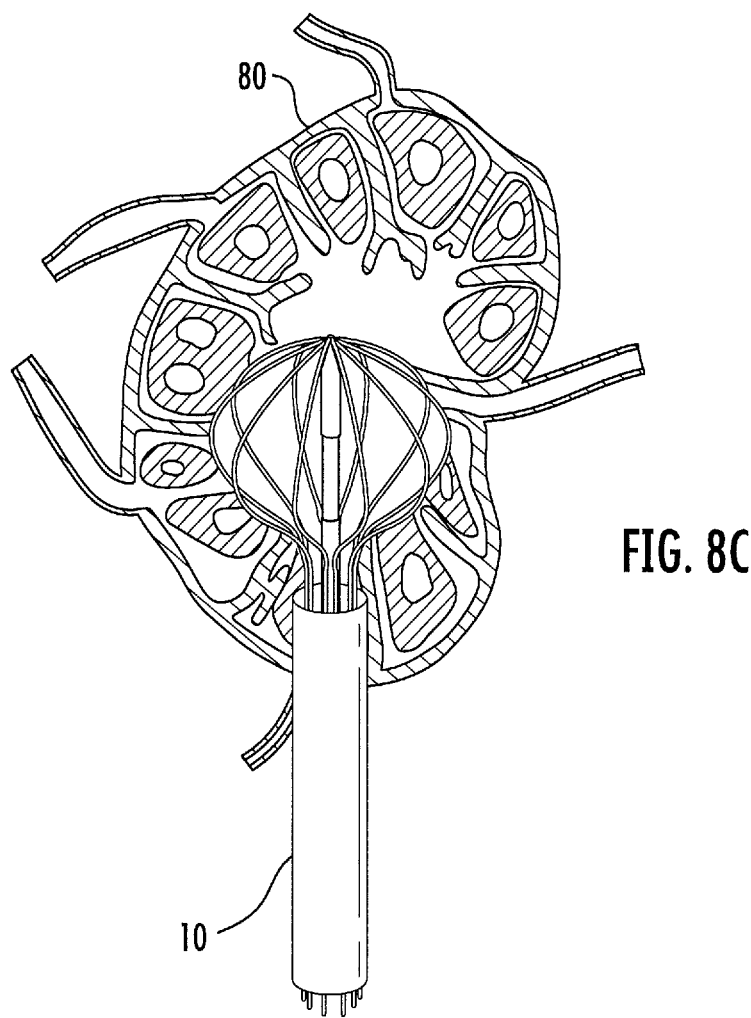
Figure 8D:
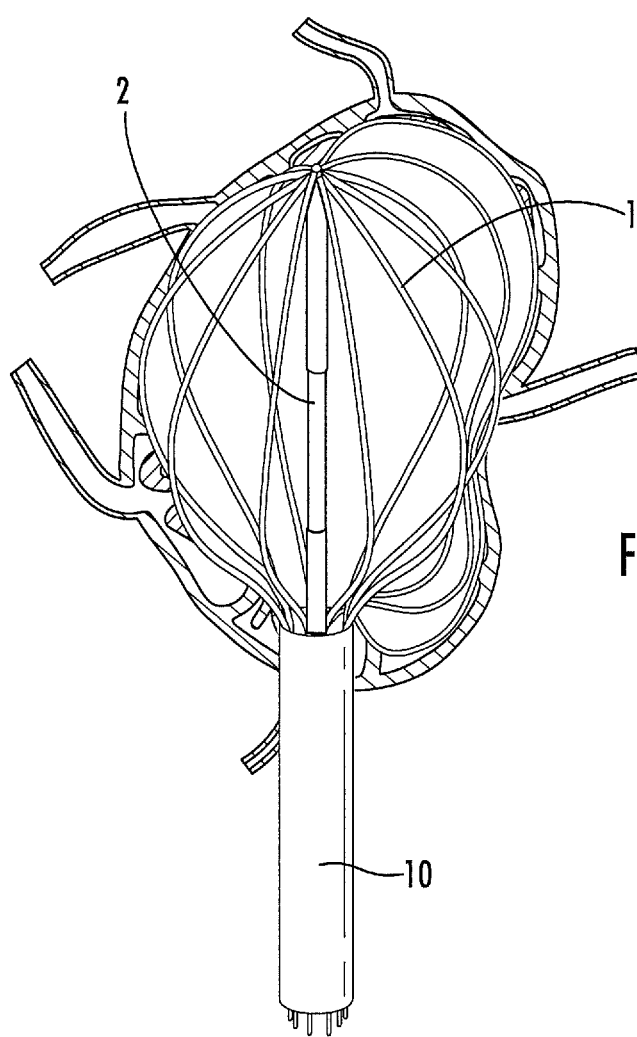
Figure 8E:
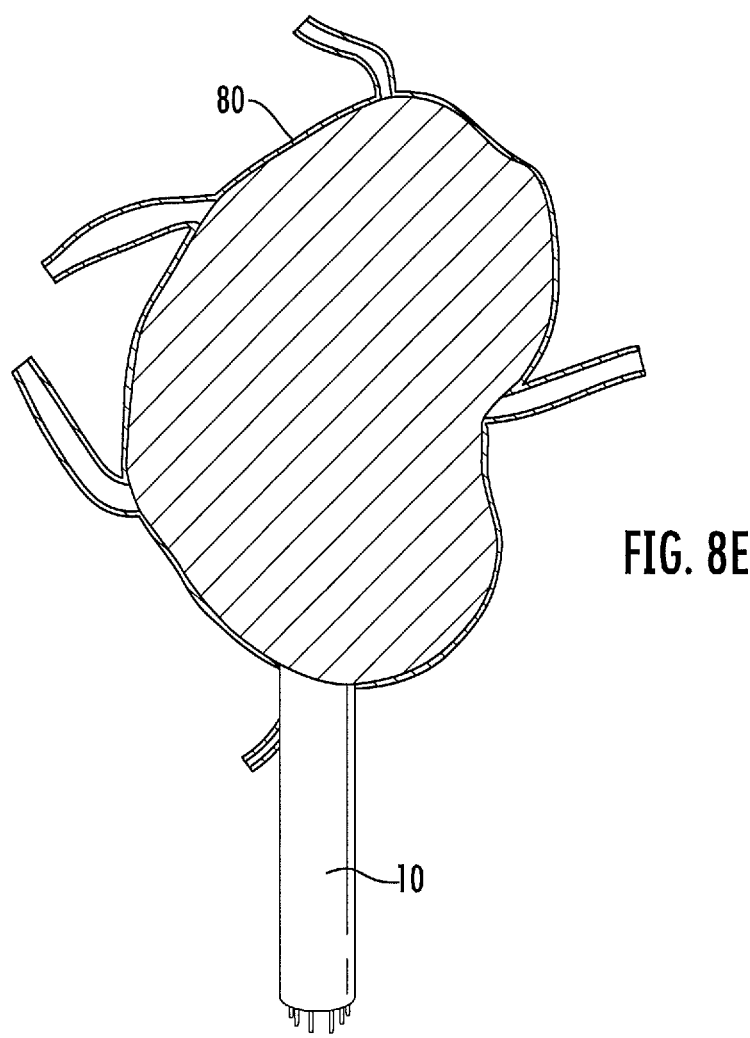

As stated above, probe 10 may be used to ablate tumors in the lymph node. FIG. 7 illustrates the locations of different lymph nodes in the human body that can be affected by different locations of a primary tumor. FIGS. 8A-8E illustrate the use of probe 10 to treat a tumor within a lymph node. More particularly, FIG. 8A illustrates an exemplary lymph node 80. FIG. 8B illustrates the insertion of probe 10 into lymph node 80. FIG. 8C illustrates the expansion of cathode cage 1 after unsheathing of cathode cage 1 and application of a DC bias between anode 2 and cathode cage 1. Fluid may also be pumped into the treatment volume defined by cathode cage 1 through apertures in the cathode 1 or anode 2 as described above. FIG. 8D illustrates further adjustment of the cathode cage 1 to contour the lymph node 80 capsule. FIG. 8E illustrates complete ablation of a lymph node indicated by the shaded area.

A coaxial ablation probe according to an embodiment of the subject matter described herein may also be used to ablate tumors in lymph nodes of the head and neck. FIG. 9A is a diagram illustrating lymph nodes of the head and neck that may be treated using a coaxial ablation probe according to the subject matter described herein. FIG. 9B is a system for treating lymph nodes of the head and neck using probe 10. The components in FIG. 9B are the same as those illustrated in FIG. 3 hence, a description thereof will not be repeated. However, probe 10 in FIG. 9B may be scaled in dimensions to treat lymph nodes, whereas the probe illustrated in FIG. 3 is scaled for size to treat liver tumors.

Although the examples described above relate primarily to ablating liver and lymph nodes, the subject matter described herein is not limited to ablating only these types of tumors. Probe 10, can be appropriately dimensioned or scaled to ablate any kind of soft tissue tumor in any region of the body where ablation is possible.

7. EXAMPLES

The following examples are merely illustrative of the presently disclosed subject matter and they should not be considered as limiting the scope of the presently disclosed subject matter in any way.

7.1 MRI Compatibility of EChT

Preliminary studies have demonstrated the safety and efficacy of the coaxial ablation probe as well as feasibility of MRI monitoring. These studies were performed with permission and in accordance with the practices of the University of Pennsylvania Institutional Review Board and Institutional Animal Care and Use Committee.
Safety and Proof of Concept:
Preliminary studies performed by the principal investigators utilized a B&K Precision 1901 DC power supply (Yorba Linda, Calif.) as the DC generator, 18 G platinum wire as the anode, and 16 G nitinol wire struts loaded into a polyether ether ketone (PEEK) needle guide to simulate the cathode cage.

In a saline model, current scatter, heating effects, and local pH measurements were dependent upon system current and NaCl concentration. Current was found to be contained within the cathode cage with current scatter <0.05 mA at 1 cm beyond the cathode cage for all saline concentrations and system settings of 2.0-5.0 A. Heat was produced at the anode with surface temperatures reaching 60° C. by 10 minutes (32 V, 2.8 A). No heat was produced at the cathode cage. Local pH changes were observed within 10 seconds with a pH of 13.8 at the cathodes and 3.2 at the anode (32 V, 2.8 A). Therefore, tissue ablation was predominantly pH mediated with no risk of current leakage.

Using a 2 cm thick ex vivo bovine liver model, ablation of 3, 4, 5, and 6 cm diameters were performed to determine the time to achieve complete ablation (FIG. 10). Complete ablation was achieved by 15 minutes for the 3 cm cage diameter, 20 minutes for the 4 cm cage diameter, 35 minutes for the 5 cm cage diameter, and 40 minutes for the 6 cm cage (32 V, 0.6-1.8 A). These rates were comparable to similarly sized RF and microwave ablations (61).
MR Monitoring:
All in situ studies were performed with permission and in accordance with the practices of the Institutional Review Board and Institutional Animal Care and Use Committee. A total of 20 MR monitored ablation was performed on eight euthanized male Yorkshire swine (25-30 kg) in a Siemens Avanto 1.5 T clinical MRI scanner with spine and body matrix coils (Malvern, Pa.). A small incision was created to place the PEEK needle guide on the liver surface. Using the needle guide, ten 16 G nitinol wire struts were arranged to create regular 3, 4 and 5 cm diameter cathode cages into a single hepatic lobe; the platinum anode was placed in the isocenter. Wire positioning was confirmed using a volumetric interpolated breath-hold examination (VIBE) T1 sequence (TR/TE 5.0/2.2 ms, FA 15°, FOV 200 mm; Matrix 196×320; slice thickness 3 mm). Custom-made insulated 12 gauge copper wire with pure copper mini-alligator clips were connected to the DC generator and fed through the wave guide to clip onto the anode and cathodes.

Coronal oblique VIBE T1 sequences were performed along the short axis of the cathode cage to serve as the monitoring sequence. Ablations were performed at each diameter up to 60 minutes (32 V, 0.2-1), with VIBE T1 monitoring sequences performed at 3-minute intervals for the 3 cm ablation and 5-minute intervals for the 4 and 5 cm ablations. Ablation completion was defined as the time at which the anode and cathode signal changes coalesced. Upon ablation completion, the struts were removed and turbo spin echo (TSE) T2 (TR/TE 5400/96 ms) and VIBE T1 sequences were obtained along the short axis of the ablation axis. The liver was subsequently explanted and the gross pathology examined.

Within the first minute of ablation, tissue necrosis was seen to develop at the anode and propagate circumferentially towards the cathode as a zone of T1 hypointense signal with a leading edge of T1 hyperintensity (FIG. 11A). Similar signal changes were observed at each cathode strut with a central T1 hypointense signal and leading edge of T1 hyperintense signal. The TSE-T2 post-ablation sequences demonstrated increased signal about the cathode cage struts, which correlated with liquefied tissue at gross pathology (FIG. 11B). Complete ablation was achieved by 15 minutes at 3 cm cage diameter, 35 minutes at 4 cm cage diameter, and 50 minutes at 5 cm diameter. Specific absorption rate (SAR) remained less than 10 W/kg for all ablations. It is important to note that all ablations were performed adjacent to the gall bladder fossa and there was no detectable damage to the gall bladder wall (FIGS. 11A and 11B).
Size and Shape Adjustment:
In situ testing of the coaxial ablation probe was performed by percutaneously placing the device into the subcapsular left hepatic lobe in three Yorkshire swine (25-30 kg). The swine were loaded in a Siemens Avanto 1.5 T clinical MRI scanner with spine and body matrix coils. A 4 mm Invivo bone biopsy trochar (Gainesville, Fla.) was used to puncture the skin to the level of the hepatic capsule. Through the defect, the device was inserted into the liver, coaxial ablation probe position was confirmed using VIBE-T1. The device was subsequently unsheathed and ablation was performed (32 V, 0.3-0.9 A) for 15 minutes to allow for self-expansion. MR monitoring was with the T1-VIBE sequence at 3 minute intervals along the short axis of the probe. Subsequently manual traction was performed to adjust the size and shape of the coaxial ablation probe. The struts opposite the hepatic capsule were advanced to direct ablation away from the hepatic capsule and ablation was allowed to continue for 6 additional minutes (FIG. 11C). Post-adjustment MRI confirms the coaxial ablation probe's ability to be size and shape adjustable.

Although the presently disclosed subject matter and its advantages have been described in detail, it should be understood that various changes, substitutions and alterations can be made herein without departing from the spirit and scope of the presently disclosed subject matter as defined by the appended claims. Moreover, the scope of the presently disclosed subject matter is not intended to be limited to the particular embodiments described in the specification. Accordingly, the appended claims are intended to include within their scope such modifications.

Patents, patent applications, publications, product descriptions, and protocols that may be cited throughout this application including in the following list of "References", the disclosures of which are incorporated herein by reference in their entireties for all purposes.

REFERENCES

1. Ahmed M, Brace C L, Lee F T, Jr., Goldberg S N. Principles of and advances in percutaneous ablation. Radiology. 2011; 258(2):351-69.
2. Knavel E M, Brace C L. Tumor ablation: common modalities and general practices. Techniques in vascular and interventional radiology. 2013; 16(4):192-200.
3. Jahangeer S, Forde P, Soden D, Hinchion J. Review of current thermal ablation treatment for lung cancer and the potential of electrochemotherapy as a means for treatment of lung tumours. Cancer treatment reviews. 2013; 39(8): 862-71.
4. Antoch G, Kuehl H, Vogt F M, Debatin J F, Stattaus J. Value of CT volume imaging for optimal placement of radiofrequency ablation probes in liver lesions. Journal of vascular and interventional radiology: JVIR. 2002; 13(11):1155-61.
5. Rose S C, Hassanein T I, Easter D W, Gamagami R A, Bouvet M, Pretorius D H, et al. Value of three-dimensional US for optimizing guidance for ablating focal liver tumors. Journal of vascular and interventional radiology: JVIR. 2001; 12(4):507-15.
6. Leveillee R J, Pease K, Salas N. Emerging needle ablation technology in urology. Current opinion in urology. 2013.
7. Ierardi A M, Floridi C, Fontana F, Chini C, Giorlando F, Piacentino F, et al. Microwave ablation of liver metastases to overcome the limitations of radiofrequency ablation. La Radiologia medica. 2013; 118(6):949-61.
8. Fabiano A J, Alberico R A. Laser-interstitial thermal therapy for refractory cerebral edema from post-radiosurgery metastasis. World neurosurgery. 2013.
9. Ellis S, Rieke V, Kohi M, Westphalen A C. Clinical applications for magnetic resonance guided high intensity focused ultrasound (MRgHIFU): present and future. Journal of medical imaging and radiation oncology. 2013; 57(4):391-9.
10. Jensen C R, Cleveland R O, Coussios C C. Real-time temperature estimation and monitoring of HIFU ablation through a combined modeling and passive acoustic mapping approach. Physics in medicine and biology. 2013; 58(17):5833-50.
11. Passera K, Selvaggi S, Scaramuzza D, Garbagnati F, Vergnaghi D, Mainardi L. Radiofrequency ablation of liver tumors: quantitative assessment of tumor coverage through CT image processing. BMC medical imaging. 2013; 13:3.
12. Robertson G S, Wemyss-Holden S A, Dennison A R, Hall P M, Baxter P, Maddern G J. Experimental study of electrolysis-induced hepatic necrosis. The British journal of surgery. 1998; 85(9):1212-6.
13. Wemyss-Holden S A, Berry D P, Robertson G S, Dennison A R, De La M H P, Maddern G J. Electrolytic ablation as an adjunct to liver resection: Safety and efficacy in patients. ANZ journal of surgery. 2002; 72(8): 589-93.
14. Wemyss-Holden S A, de la M H P, Robertson G S, Dennison A R, Vanderzon P S, Maddern G J. The safety of electrolytically induced hepatic necrosis in a pig model. The Australian and New Zealand journal of surgery. 2000; 70(8):607-12.
15. Wemyss-Holden S A, Dennison A R, Finch G J, Hall Pd Pde L, Maddern G J. Electrolytic ablation as an adjunct to liver resection: experimental studies of predictability and safety. The British journal of surgery. 2002; 89(5):579-85.
16. Wemyss-Holden S A, Robertson G S, Dennison A R, de la M H P, Fothergill J C, Jones B, et al. Electrochemical lesions in the rat liver support its potential for treatment of liver tumors. The Journal of surgical research. 2000; 93(1):55-62.
17. Wemyss-Holden S A, Robertson G S, Dennison A R, Vanderzon P S, Hall P M, Maddern G J. A new treatment for unresectable liver tumours: long-term studies of electrolytic lesions in the pig liver. Clinical science. 2000; 98(5):561-7.
18. Wemyss-Holden S A, Robertson G S, Hall P D, Dennison A R, Maddern G J. Electrolytic treatment of colorectal liver tumour deposits in a rat model: a technique with potential for patients with unresectable liver tumours. Digestive diseases. 2000; 18(2):50-7.
19. Finch J G, Fosh B, Anthony A, Slimani E, Texler M, Berry D P, et al. Liver electrolysis: pH can reliably monitor the extent of hepatic ablation in pigs. Clinical science. 2002; 102(4):389-95.
20. Fosh B G, Finch J G, Anthony A A, Lea M M, Wong S K, Black C L, et al. Use of electrolysis for the treatment of non-resectable hepatocellular carcinoma. ANZ journal of surgery. 2003; 73(12):1068-70.
21. Nilsson E, von Euler H, Berendson J, Thorne A, Wersall P, Naslund I, et al. Electrochemical treatment of tumours. Bioelectrochemistry. 2000; 51(1):1-11.
22. von Euler H, Nilsson E, Olsson J M, Lagerstedt A S. Electrochemical treatment (EChT) effects in rat mammary and liver tissue. In vivo optimizing of a dose-planning model for EChT of tumours. Bioelectrochemistry. 2001; 54(2):117-24.
23. von Euler H, Olsson J M, Hultenby K, Thorne A, Lagerstedt A S. Animal models for treatment of unresectable liver tumours: a histopathologic and ultra-structural study of cellular toxic changes after electrochemical treatment in rat and dog liver. Bioelectrochemistry. 2003; 59(1-2):89-98.
24. von Euler H, Soderstedt A, Thorne A, Olsson J M, Yongqing G. Cellular toxicity induced by different pH levels on the R3230AC rat mammary tumour cell line. An in vitro model for investigation of the tumour destructive properties of electrochemical treatment of tumours. Bioelectrochemistry. 2002; 58(2):163-70.
25. Martin J, Athreya S. Meta-analysis of cryoablation versus microwave ablation for small renal masses: is there a difference in outcome? Diagnostic and interventional radiology. 2013; 19(6):501-7.
26. Autorino R, Kaouk J H. Cryoablation for small renal tumors: current status and future perspectives. Urologic oncology. 2012; 30(4 Suppl):S20-7.
27. Paiva M B, Joo J, Abrahao M, Ribeiro J C, Cervantes O, Sercarz J A. Update on laser photochemotherapy: an alternative for cancer treatment. Anti-cancer agents in medicinal chemistry. 2011; 11(8):772-9.

28. Froeling V, Meckelburg K, Schreiter N F, Scheurig-Muenkler C, Kamp J, Maurer M H, et al. Outcome of uterine artery embolization versus MR-guided high-intensity focused ultrasound treatment for uterine fibroids: Long-term results. European journal of radiology. 2013; 82(12):2265-9.
29. Jenne J W, Preusser T, Gunther M. High-intensity focused ultrasound: principles, therapy guidance, simulations and applications. Zeitschrift fur medizinische Physik. 2012; 22(4):311-22.
30. Napoli A, Anzidei M, De Nunzio C, Cartocci G, Panebianco V, De Dominicis C, et al. Real-time magnetic resonance-guided high-intensity focused ultrasound focal therapy for localised prostate cancer: preliminary experience. European urology. 2013; 63(2):395-8.
31. Bruix J, Boix L, Sala M, Llovet J M. Focus on hepatocellular carcinoma. Cancer cell. 2004; 5(3):215-9.
32. Bockris J O M, Khan S U M. Surface electrochemistry: a molecular level approach. New York: Plenum; 1993. xxxii, 1014 p. p.
33. Samuelsson L, Olin T, Berg N O. Electrolytic destruction of lung tissue in the rabbit. Acta radiologica: diagnosis. 1980; 21(4):447-54.
34. Griffin D T, Dodd N J, Moore J V, Pullan B R, Taylor T V. The effects of low-level direct current therapy on a preclinical mammary carcinoma: tumour regression and systemic biochemical sequelae. British journal of cancer. 1994; 69(5):875-8.
35. Griffin D T, Dodd N J, Zhao S, Pullan B R, Moore J V. Low-level direct electrical current therapy for hepatic metastases. I. Preclinical studies on normal liver. British journal of cancer. 1995; 72(1):31-4.
36. Nilsson E, Fontes E. Mathematical modelling of physicochemical reactions and transport processes occurring around a platinum cathode during the electrochemical treatment of tumours. Bioelectrochemistry. 2001; 53(2):213-24.
37. Lin X Z, Jen C M, Chou C K, Chou C S, Sung M J, Chou T C. Saturated saline enhances the effect of electrochemical therapy. Digestive diseases and sciences. 2000; 45(3):509-14.
38. Chou C K, McDougall J A, Ahn C, Vora N. Electrochemical treatment of mouse and rat fibrosarcomas with direct current. Bioelectromagnetics. 1997; 18(1):14-24.
39. Li K, Xin Y, Gu Y, Xu B, Fan D, Ni B. Effects of direct current on dog liver: possible mechanisms for tumor electrochemical treatment. Bioelectromagnetics. 1997; 18(1):2-7.
40. Ciria H C, Quevedo M S, Cabrales L B, Bruzon R P, Salas M F, Pena O G, et al. Antitumor effectiveness of different amounts of electrical charge in Ehrlich and fibrosarcoma Sa-37 tumors. BMC cancer. 2004; 4:87.
41. Ciria H M, Gonzalez M M, Zamora L O, Cabrales L E, Sierra Gonzalez G V, de Oliveira L O, et al. Antitumor effects of electrochemical treatment. Chinese journal of cancer research 2013; 25(2):223-34.
42. Schroeppel E A, Kroll K, Damon M C, Kroll A A. Direct current ablation destroys multi-stage fibrosarcomas in rats. Conference proceedings: Annual International Conference of the IEEE Engineering in Medicine and Biology Society IEEE Engineering in Medicine and Biology Society Conference. 2009; 2009:3099-104.
43. Czymek R, Dinter D, Loffler S, Gebhard M, Laubert T, Lubienski A, et al. Electrochemical treatment: An investigation of dose-response relationships using an isolated liver perfusion model. Saudi journal of gastroenterology: official journal of the Saudi Gastroenterology Association. 2011; 17(5):335-42.
44. Brown D B, Narayanan G. Interventional radiology and the pancreatic cancer patient. Cancer journal. 2012; 18(6):591-601.
45. Yu Z, Zhang X, Ren P, Zhang M, Qian J. Therapeutic potential of irreversible electroporation in sarcoma. Expert review of anticancer therapy. 2012; 12(2):177-84.
46. Appelbaum L, Ben-David E, Faroja M, Nissenbaum Y, Sosna J, Goldberg S N. Irreversible Electroporation Ablation: Creation of Large-Volume Ablation Zones in in Vivo Porcine Liver with Four-Electrode Arrays. Radiology. 2013.
47. Niessen C, Jung E M, Wohlgemuth W A, Trabold B, Haimerl M, Schreyer A, et al. Irreversible electroporation of a hepatocellular carcinoma lesion adjacent to a transjugular intrahepatic portosystemic shunt stent graft. Korean journal of radiology: official journal of the Korean Radiological Society. 2013; 14(5):797-800.
48. Martin R C. Irreversible electroporation of locally advanced pancreatic head adenocarcinoma. Journal of gastrointestinal surgery: official journal of the Society for Surgery of the Alimentary Tract. 2013; 17(10):1850-6.
49. Ben-David E, Appelbaum L, Sosna J, Nissenbaum I, Goldberg S N. Characterization of irreversible electroporation ablation in in vivo porcine liver. AJR American journal of roentgenology. 2012; 198(1):W62-8.
50. Ben-David E, Ahmed M, Faroja M, Moussa M, Wandel A, Sosna J, et al. Irreversible electroporation: treatment effect is susceptible to local environment and tissue properties. Radiology. 2013; 269(3):738-47.
51. Lu D S, Kee S T, Lee E W. Irreversible electroporation: ready for prime time? Techniques in vascular and interventional radiology. 2013; 16(4):277-86.
52. Guo Y, Zhang Y, Nijm G M, Sahakian A V, Yang G Y, Omary R A, et al. Irreversible electroporation in the liver: contrast-enhanced inversion-recovery MR imaging approaches to differentiate reversibly electroporated penumbra from irreversibly electroporated ablation zones. Radiology. 2011; 258(2):461-8.
53. Ormiga F, da Cunha Ponciano Gomes J A, de Araujo M C, Barbosa A O. An initial investigation of the electrochemical dissolution of fragments of nickel-titanium endodontic files. Journal of endodontics. 2011; 37(4):526-30.
54. Castleman L S, Motzkin S M, Alicandri F P, Bonawit V L. Biocompatibility of nitinol alloy as an implant material. Journal of biomedical materials research. 1976; 10(5):695-731.
55. Civjan S, Huget E F, DeSimon L B. Potential applications of certain nickel-titanium (nitinol) alloys. Journal of dental research. 1975; 54(1):89-96.
56. Simon M, Kaplow R, Salzman E, Freiman D. A vena cava filter using thermal shape memory alloy. Experimental aspects. Radiology. 1977; 125(1):87-94.
57. Girard M J, Hahn P F, Saini S, Dawson S L, Goldberg M A, Mueller P R. Wallstent metallic biliary endoprosthesis: MR imaging characteristics. Radiology. 1992; 184(3):874-6.
58. Buehler W J, Gilfrich J V, Wiley R C. Effects of low-temperature phase changes on the mechanical properties of alloys near composition TiNi, J Appl Phys. 1963; 34:3.
59. Wang F E, Buehler W J, Pickart S J. Crystal structure and a unique martensitic transition of TiNi. J Appl Phys. 1965; 36:8.

60. Yueng K W K, Cheung K M C, Lu W W, Chung C Y. Materials Science and Engineering. Optimization of thermal treatment parameters to alter austenitic phase transition temperature of NiTi alloy for medical implant. Lausanne, Switzerland: Elsevier Sequoia; 1988. p. 213-8.

61. Correa-Gallego C, Fong Y, Gonen M, D'Angelica M I, Allen P J, DeMatteo R P, et al. A Retrospective Comparison of Microwave Ablation vs. Radiofrequency Ablation for Colorectal Cancer Hepatic Metastases. Ann Surg Oncol. 2014; 21(13):4278-83.

What is claimed is:

1. A coaxial ablation probe for percutaneous ablation, the coaxial ablation probe comprising:
    an anode;
    a cathode cage surrounding the anode, the cathode cage including a plurality of struts, wherein the anode extends coaxially with respect to the struts that form the cathode cage and wherein the cathode cage defines an ablation volume;
    an outer sheath for surrounding at least a portion of the cathode cage, wherein the sheath is movable from a first position for compressing the struts into a patient insertion position and a second position for allowing expansion of the struts to a treatment position, wherein the sheath includes channels through which the struts extend; and
    a plurality of actuators coupled to the struts and movable within the sheath to allow individual radial expansion and contraction of each strut.

2. The coaxial ablation probe of claim 1 wherein the channels are open.

3. The coaxial ablation probe of claim 1 wherein the channels are closed.

4. The coaxial ablation probe of claim 1 wherein the sheath includes grooves in which the actuators are movable and wherein the grooves include teeth for locking the actuators in axial positions corresponding to desired strut expansion or contraction.

5. The coaxial ablation probe of claim 1 wherein the sheath is substantially uniform in diameter.

6. The coaxial ablation probe of claim 1 wherein the sheath has a first diameter at a patient insertion end and a second diameter opposite the patient insertion end, the first diameter being less than the second diameter.

7. The coaxial ablation probe of claim 1 wherein the cathode cage defines a closed treatment volume.

8. The coaxial ablation probe of claim 1 wherein the cathode cage defines an open treatment volume.

9. The coaxial ablation probe of claim 1 comprising support struts extending between the struts and the cathode cage.

10. The coaxial ablation probe of claim 1 wherein the struts comprise wires.

11. The coaxial ablation probe of claim 1 wherein the struts comprise hollow tubes and include apertures formed in at least some of the tubes to allow fluid to flow into the treatment volume.

12. The coaxial ablation probe of claim 1 wherein each strut has a generally polygonal radial cross section.

13. A coaxial ablation probe for percutaneous ablation, the coaxial ablation probe comprising:
    an anode, wherein the anode comprises a wire; and
    a cathode cage surrounding the anode, the cathode cage including a plurality of struts, wherein the anode extends coaxially with respect to the struts that form the cathode cage and wherein the cathode cage defines an ablation volume.

14. The coaxial ablation probe of claim 1 wherein the anode includes a plurality of struts that define a closed volume.

15. The coaxial ablation probe of claim 1 wherein the anode includes a plurality of struts that define an open volume.

16. The coaxial ablation probe of claim 1 wherein the anode comprises a hollow elongate member with apertures to allow fluid flow from within the anode into the treatment volume.

17. The coaxial ablation probe of claim 1 wherein the anode comprises a needle-like member.

18. The coaxial ablation probe of claim 1 wherein the anode comprises a wire surrounded by a hollow tube with apertures in the tube to allow electrolyte flow from within the tube into the treatment volume.

19. The coaxial ablation probe of claim 1 wherein the struts are cut from a tube.

20. The coaxial ablation probe of claim 1 wherein the struts are cut from a tube but are axially separated from each other at one end and are individually adjustable.

21. The coaxial ablation probe of claim 1 wherein the struts form a tissue anchor on one end of the probe.

22. A method for percutaneous ablation, the method comprising:
    inserting a coaxial ablation probe into a patient;
    the coaxial ablation probe comprising a cathode cage surrounding an anode, the cathode cage including the plurality of struts and the anode extending coaxially with respect to the struts that form the cathode cage;
    applying a DC voltage between the anode and the cathode cage;
    monitoring tissue ablation in a volume defined by the cathode cage; and
    withdrawing the probe upon ablation of a desired target wherein withdrawing the probe comprises:
    individually contracting any individually extended struts;
    sheathing the cathode cage;
    removing the probe through a probe entry tract; and
    ablating tissue in the probe entry tract to reduce bleeding.

23. The method of claim 22 comprising expanding the cathode cage to define a treatment volume.

24. The method of claim 23 comprising pumping a fluid into the treatment volume.

25. The method of claim 24 wherein pumping the fluid into the treatment volume includes pumping the fluid through apertures in the anode and/or the struts that define the cathode cage.

26. The method of claim 25 comprising withdrawing fluid from the volume defined by the cathode cage through the apertures.

27. The method of claim 22 wherein monitoring the treatment includes monitoring real time or near real time magnetic resonance images of the treatment volume.

* * * * *

UNITED STATES PATENT AND TRADEMARK OFFICE
CERTIFICATE OF CORRECTION

PATENT NO. : 10,314,648 B2
APPLICATION NO. : 15/104142
DATED : June 11, 2019
INVENTOR(S) : Ge et al.

Page 1 of 1

It is certified that error appears in the above-identified patent and that said Letters Patent is hereby corrected as shown below:

On the Title Page

Item (73) Assignee:
Replace "Universoty"
With --University--

Signed and Sealed this
Third Day of September, 2019

Andrei Iancu
*Director of the United States Patent and Trademark Office*